(12) United States Patent
Ginn et al.

(10) Patent No.: US 9,050,087 B2
(45) Date of Patent: Jun. 9, 2015

(54) INTEGRATED VASCULAR DEVICE WITH PUNCTURE SITE CLOSURE COMPONENT AND SEALANT AND METHODS OF USE

(75) Inventors: Richard S. Ginn, San Jose, CA (US); W. Martin Belef, San Jose, CA (US)

(73) Assignee: INTEGRATED VASCULAR SYSTEMS, INC., Sunnyvale, CA (US)

( * ) Notice: Subject to any disclaimer, the term of this patent is extended or adjusted under 35 U.S.C. 154(b) by 6 days.

(21) Appl. No.: 12/106,937

(22) Filed: May 14, 2008

(65) Prior Publication Data
US 2008/0221616 A1 Sep. 11, 2008

Related U.S. Application Data

(60) Division of application No. 10/147,774, filed on May 17, 2002, now Pat. No. 7,931,669, which is a continuation of application No. 09/610,238, filed on Jul. 5, 2000, now Pat. No. 6,391,048, which is a continuation-in-part of application No. 09/478,179, filed on Jan. 5, 2000, now Pat. No. 6,197,042.

(51) Int. Cl.
*A61B 17/08* (2006.01)
*A61B 17/10* (2006.01)
(Continued)

(52) U.S. Cl.
CPC ........... *A61B 17/10* (2013.01); *A61B 17/00491* (2013.01); *A61B 17/0057* (2013.01); *A61B 17/064* (2013.01); *A61B 17/0643* (2013.01); *A61B 17/083* (2013.01); *A61B 17/128* (2013.01); *A61B 17/1285* (2013.01); *A61B 2017/00637* (2013.01); *A61B 2017/00663* (2013.01); *A61B 2017/00668* (2013.01);
(Continued)

(58) Field of Classification Search
CPC ................. A61B 17/0057; A61B 2017/00646; A61B 17/00491; A61B 2017/00862; A61B 2017/00663; A61B 17/085
USPC .................. 606/213; 623/13.11–13.15, 14.12
See application file for complete search history.

(56) References Cited

U.S. PATENT DOCUMENTS

| 287,046 A | 10/1883 | Norton |
| 438,400 A | 10/1890 | Brennen |

(Continued)

FOREIGN PATENT DOCUMENTS

| AU | 2003297432 | 12/2003 |
| CA | 2 339 060 | 2/2000 |

(Continued)

OTHER PUBLICATIONS

U.S. Appl. No. 10/264,306, May 26, 2005, Office Action.
(Continued)

*Primary Examiner* — Gregory Anderson
*Assistant Examiner* — Christina Lauer
(74) *Attorney, Agent, or Firm* — Workman Nydegger; Randy Shen

(57) ABSTRACT

Apparatus and methods are provided for use in sealing a vascular puncture site. The invention comprises an integrated vascular device having a sheath with a closure component and puncture sealant. The closure component is disposed on and advanceable over the exterior of the sheath and may comprise any of a variety of apparatus suited for closing a vascular puncture. Once the closure component has been actuated to close the puncture, sealant is introduced to seal the puncture. The sheath and closure component are then removed from the patient.

15 Claims, 5 Drawing Sheets

(51) Int. Cl.
*A61B 17/128* (2006.01)
*A61B 17/00* (2006.01)
*A61B 17/064* (2006.01)
*A61M 25/06* (2006.01)

(52) U.S. Cl.
CPC ............. *A61B2017/00672* (2013.01); *A61B 2017/00862* (2013.01); *A61B 2017/0641* (2013.01); *A61M 25/0662* (2013.01)

(56) References Cited

U.S. PATENT DOCUMENTS

| | | |
|---|---|---|
| 556,082 A | 3/1896 | Boeddinghaus |
| 1,088,393 A | 2/1914 | Backus |
| 1,123,290 A | 1/1915 | Von Herff |
| 1,242,139 A | 10/1917 | Callahan |
| 1,331,401 A | 2/1920 | Summers |
| 1,426,111 A | 8/1922 | Sacker |
| 1,480,935 A | 1/1924 | Gleason |
| 1,516,990 A | 11/1924 | Silverman |
| 1,596,004 A | 8/1926 | De Bengoa |
| 1,647,958 A | 11/1927 | Ciarlante |
| 1,847,347 A | 3/1932 | Maisto |
| 1,852,098 A | 4/1932 | Anderson |
| 1,880,569 A | 10/1932 | Weis |
| 2,075,508 A | 3/1937 | Davidson |
| 2,087,074 A | 7/1937 | Tucker |
| 2,108,206 A | 2/1938 | Meeker |
| 2,210,061 A | 8/1940 | Caminez |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,610,631 A | 9/1952 | Calicchio |
| 2,684,070 A | 7/1954 | Kelsey |
| 2,755,699 A | 7/1956 | Forster |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,014,483 A | 12/1961 | McCarthy |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,348,595 A | 10/1967 | Stevens, Jr. |
| 3,357,070 A | 12/1967 | Sloan |
| 3,482,428 A | 12/1969 | Kapitanov et al. |
| 3,494,533 A | 2/1970 | Green et al. |
| 3,510,923 A | 5/1970 | Blake |
| 3,513,848 A | 5/1970 | Winston et al. |
| 3,523,351 A | 8/1970 | Filia |
| 3,525,340 A | 8/1970 | Gilbert |
| 3,586,002 A | 6/1971 | Wood |
| 3,604,425 A | 9/1971 | Le Roy |
| 3,618,447 A | 11/1971 | Goins |
| 3,664,345 A | 5/1972 | Dabbs et al. |
| 3,677,243 A | 7/1972 | Nerz |
| 3,682,180 A | 8/1972 | McFarlane |
| 3,732,719 A | 5/1973 | Pallotta |
| 3,750,650 A | 8/1973 | Ruttgers |
| 3,753,438 A | 8/1973 | Wood et al. |
| 3,757,629 A | 9/1973 | Schneider |
| 3,805,337 A | 4/1974 | Branstetter |
| 3,814,104 A | 6/1974 | Irnich et al. |
| 3,823,719 A | 7/1974 | Cummings |
| 3,828,791 A | 8/1974 | Santos |
| 3,831,608 A | 8/1974 | Kletschka et al. |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,931,821 A | 1/1976 | Kletschka et al. |
| 3,939,820 A | 2/1976 | Grayzel |
| 3,944,114 A | 3/1976 | Coppens |
| 3,960,147 A | 6/1976 | Murray |
| 3,976,079 A | 8/1976 | Samuels et al. |
| 3,985,138 A | 10/1976 | Jarvik |
| 4,007,743 A | 2/1977 | Blake |
| 4,011,872 A | 3/1977 | Komiya |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,189,808 A | 2/1980 | Brown |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,267,995 A | 5/1981 | McMillan |
| 4,273,129 A | 6/1981 | Boebel |
| 4,274,415 A | 6/1981 | Kanamoto et al. |
| 4,278,091 A | 7/1981 | Borzone |
| 4,287,489 A | 9/1981 | Pinkham |
| 4,291,698 A | 9/1981 | Fuchs et al. |
| 4,317,445 A | 3/1982 | Robinson |
| 4,317,451 A | 3/1982 | Cerwin et al. |
| 4,318,401 A | 3/1982 | Zimmerman |
| 4,327,485 A | 5/1982 | Rix |
| 4,345,606 A | 8/1982 | Littleford |
| 4,359,052 A | 11/1982 | Staub |
| 4,368,736 A | 1/1983 | Kaster |
| 4,387,489 A | 6/1983 | Dudek |
| 4,396,139 A | 8/1983 | Hall et al. |
| 4,400,879 A | 8/1983 | Hildreth |
| 4,407,286 A | 10/1983 | Noiles et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| 4,501,276 A | 2/1985 | Lombardi |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Valaincourt |
| 4,526,174 A | 7/1985 | Froehlich |
| 4,577,635 A | 3/1986 | Meredith |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,644,956 A | 2/1987 | Morgenstern |
| 4,651,737 A | 3/1987 | Deniega |
| 4,664,305 A | 5/1987 | Blake, III et al. |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |

(56) References Cited

U.S. PATENT DOCUMENTS

| | | |
|---|---|---|
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froelich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,009,663 A | 4/1991 | Broomé |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,071,430 A | 12/1991 | de Salis et al. |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A * | 10/1992 | Nakao et al. ................. 606/142 |
| 5,158,566 A | 10/1992 | Pianetti |
| 5,160,339 A | 11/1992 | Chen et al. |
| 5,163,343 A | 11/1992 | Gish |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,171,259 A | 12/1992 | Inoue |
| 5,176,648 A | 1/1993 | Holmes et al. |
| 5,176,682 A | 1/1993 | Chow |
| 5,176,691 A | 1/1993 | Pierce |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,203,787 A | 4/1993 | Noblitt et al. |
| 5,207,697 A | 5/1993 | Carusillo et al. |
| 5,209,756 A | 5/1993 | Seedhorm et al. |
| 5,217,024 A | 6/1993 | Dorsey et al. |
| 5,217,471 A | 6/1993 | Burkhart |
| 5,219,359 A | 6/1993 | McQuilkin et al. |
| 5,222,971 A | 6/1993 | Willard et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,237,996 A | 8/1993 | Waldman |
| 5,242,456 A | 9/1993 | Nash et al. |
| 5,242,457 A | 9/1993 | Akopov et al. |
| 5,242,459 A | 9/1993 | Buelna |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,258,015 A | 11/1993 | Li et al. |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,282,832 A | 2/1994 | Toso et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,306,280 A | 4/1994 | Bregen et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A * | 11/1994 | Gordon ................. 606/144 |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,897 A | 1/1995 | Wholey |
| 5,383,905 A | 1/1995 | Golds et al. |
| RE34,866 E | 2/1995 | Kensey et al. |
| 5,391,173 A | 2/1995 | Wilk |
| 5,392,978 A | 2/1995 | Velez |
| 5,395,030 A | 3/1995 | Kuramoto et al. |
| 5,403,330 A | 4/1995 | Tuason |
| 5,403,331 A | 4/1995 | Chesterfield et al. |
| 5,404,621 A | 4/1995 | Heinke |
| 5,409,499 A | 4/1995 | Yi |

(56) References Cited

U.S. PATENT DOCUMENTS

| | | | |
|---|---|---|---|
| 5,411,520 A | 5/1995 | Nash et al. | |
| 5,413,571 A | 5/1995 | Katsaros et al. | |
| 5,413,584 A | 5/1995 | Schulze | |
| 5,416,584 A | 5/1995 | Kay | |
| 5,417,699 A | 5/1995 | Klein et al. | |
| 5,419,765 A | 5/1995 | Weldon et al. | |
| 5,419,777 A | 5/1995 | Hofling | |
| 5,421,832 A | 6/1995 | Lefebvre | |
| 5,423,857 A | 6/1995 | Rosenman et al. | |
| 5,425,489 A * | 6/1995 | Shichman et al. | 227/108 |
| 5,425,740 A | 6/1995 | Hutchinson, Jr. | |
| 5,431,639 A | 7/1995 | Shaw | |
| 5,431,667 A | 7/1995 | Thompson et al. | |
| 5,433,721 A | 7/1995 | Hooven et al. | |
| 5,437,631 A | 8/1995 | Janzen | |
| 5,439,479 A | 8/1995 | Shichman et al. | |
| 5,443,477 A | 8/1995 | Marin et al. | |
| 5,443,481 A | 8/1995 | Lee | |
| 5,445,167 A | 8/1995 | Yoon et al. | |
| 5,449,359 A | 9/1995 | Groiso | |
| 5,451,235 A | 9/1995 | Lock et al. | |
| 5,456,400 A | 10/1995 | Shichman et al. | |
| 5,462,558 A | 10/1995 | Kolesa et al. | |
| 5,462,561 A | 10/1995 | Voda | |
| 5,464,413 A | 11/1995 | Siska, Jr. et al. | |
| 5,466,241 A | 11/1995 | Leroy et al. | |
| 5,470,010 A | 11/1995 | Rothfuss et al. | |
| 5,471,982 A | 12/1995 | Edwards et al. | |
| 5,474,557 A | 12/1995 | Mai | |
| 5,474,569 A | 12/1995 | Zinreich et al. | |
| 5,474,572 A | 12/1995 | Hayhurst | |
| 5,476,505 A | 12/1995 | Limon | |
| 5,478,352 A | 12/1995 | Fowler | |
| 5,478,353 A | 12/1995 | Yoon | |
| 5,478,354 A | 12/1995 | Tovey et al. | |
| 5,486,195 A | 1/1996 | Myers et al. | |
| 5,492,119 A | 2/1996 | Abrams | |
| 5,496,332 A | 3/1996 | Sierra et al. | |
| 5,497,933 A | 3/1996 | DeFonzo et al. | |
| 5,501,698 A | 3/1996 | Roth et al. | |
| 5,507,744 A | 4/1996 | Tay et al. | |
| 5,507,755 A | 4/1996 | Gresl et al. | |
| 5,510,115 A | 4/1996 | Breillatt, Jr. et al. | |
| 5,514,159 A | 5/1996 | Matula et al. | |
| 5,521,184 A | 5/1996 | Zimmermann | |
| 5,522,840 A | 6/1996 | Krajicek | |
| 5,527,322 A | 6/1996 | Klein et al. | |
| 5,536,251 A | 7/1996 | Evard et al. | |
| 5,536,267 A | 7/1996 | Edwards | |
| 5,540,712 A | 7/1996 | Kleshinski et al. | |
| 5,540,716 A | 7/1996 | Hlavacek | |
| 5,543,520 A | 8/1996 | Zimmermann | |
| 5,544,802 A | 8/1996 | Crainich | |
| 5,547,474 A | 8/1996 | Kloeckl et al. | |
| 5,560,532 A | 10/1996 | DeFonzo et al. | |
| 5,562,684 A | 10/1996 | Kammerer | |
| 5,571,120 A | 11/1996 | Yoon | |
| 5,573,540 A | 11/1996 | Yoon | |
| 5,573,784 A | 11/1996 | Badylak et al. | |
| 5,575,771 A | 11/1996 | Walinsky | |
| 5,582,616 A | 12/1996 | Bolduc et al. | |
| 5,584,879 A | 12/1996 | Reimold et al. | |
| 5,591,205 A | 1/1997 | Fowler | |
| 5,593,412 A | 1/1997 | Martinez et al. | |
| 5,593,422 A | 1/1997 | Muijs Van de Moer et al. | |
| 5,593,425 A | 1/1997 | Bonutti et al. | |
| 5,601,602 A | 2/1997 | Fowler | |
| 5,609,597 A | 3/1997 | Lehrer | |
| 5,611,986 A | 3/1997 | Datta et al. | |
| 5,613,974 A | 3/1997 | Andreas et al. | |
| 5,613,975 A | 3/1997 | Christy | |
| 5,618,291 A | 4/1997 | Thompson et al. | |
| 5,618,306 A | 4/1997 | Roth et al. | |
| 5,620,452 A | 4/1997 | Yoon | |
| 5,620,461 A | 4/1997 | Muijs et al. | |
| 5,626,614 A | 5/1997 | Hart | |
| 5,630,824 A | 5/1997 | Hart | |
| 5,634,936 A | 6/1997 | Lindon et al. | |
| 5,643,318 A | 7/1997 | Tsukernik et al. | |
| 5,645,553 A | 7/1997 | Kolesa et al. | |
| 5,645,565 A | 7/1997 | Rudd et al. | |
| 5,645,566 A | 7/1997 | Brenneman et al. | |
| 5,645,567 A | 7/1997 | Crainich | |
| 5,647,372 A | 7/1997 | Tovey et al. | |
| 5,649,959 A | 7/1997 | Hannam et al. | |
| D383,539 S | 9/1997 | Croley | |
| 5,669,917 A | 9/1997 | Sauer et al. | |
| 5,669,935 A | 9/1997 | Rosenman et al. | |
| 5,672,174 A | 9/1997 | Gough et al. | |
| 5,674,231 A | 10/1997 | Green et al. | |
| 5,676,689 A | 10/1997 | Kensey et al. | |
| 5,676,974 A | 10/1997 | Valdes et al. | |
| 5,681,280 A | 10/1997 | Rusk et al. | |
| 5,681,334 A | 10/1997 | Evans et al. | |
| 5,681,351 A | 10/1997 | Jamiolkowski et al. | |
| 5,683,405 A | 11/1997 | Yacoubian et al. | |
| 5,690,674 A | 11/1997 | Diaz | |
| 5,693,061 A | 12/1997 | Pierce et al. | |
| 5,695,504 A | 12/1997 | Gifford, III et al. | |
| 5,695,505 A | 12/1997 | Yoon | |
| 5,695,524 A | 12/1997 | Kelley et al. | |
| 5,697,943 A | 12/1997 | Sauer et al. | |
| 5,700,273 A | 12/1997 | Buelna et al. | |
| 5,709,224 A | 1/1998 | Behl et al. | |
| 5,709,708 A | 1/1998 | Thal | |
| 5,713,899 A | 2/1998 | Marnay et al. | |
| 5,715,987 A | 2/1998 | Kelley et al. | |
| 5,716,375 A | 2/1998 | Fowler | |
| 5,720,755 A | 2/1998 | Dakov | |
| 5,720,765 A | 2/1998 | Thal | |
| 5,725,498 A | 3/1998 | Janzen et al. | |
| 5,725,552 A | 3/1998 | Kotula et al. | |
| 5,725,554 A | 3/1998 | Simon et al. | |
| 5,725,556 A | 3/1998 | Moser et al. | |
| 5,728,109 A | 3/1998 | Schulze et al. | |
| 5,728,110 A | 3/1998 | Vidal et al. | |
| 5,728,114 A | 3/1998 | Evans et al. | |
| 5,728,116 A | 3/1998 | Rosenman | |
| 5,728,122 A | 3/1998 | Leschinsky et al. | |
| 5,728,132 A | 3/1998 | Van Tassel et al. | |
| 5,728,133 A | 3/1998 | Kontos | |
| 5,728,143 A | 3/1998 | Gough et al. | |
| 5,732,872 A | 3/1998 | Bolduc et al. | |
| 5,735,736 A | 4/1998 | Volk | |
| 5,735,873 A | 4/1998 | MacLean | |
| 5,735,875 A | 4/1998 | Bonutti et al. | |
| 5,735,877 A | 4/1998 | Pagedas | |
| 5,749,826 A | 5/1998 | Faulkner | |
| 5,749,898 A | 5/1998 | Schulze et al. | |
| 5,752,966 A | 5/1998 | Chang | |
| 5,755,726 A | 5/1998 | Pratt et al. | |
| 5,755,727 A | 5/1998 | Kontos | |
| 5,755,778 A | 5/1998 | Kleshinski | |
| 5,759,189 A | 6/1998 | Ferragamo et al. | |
| 5,766,217 A | 6/1998 | Christy | |
| 5,766,246 A | 6/1998 | Mulhauser et al. | |
| 5,769,862 A | 6/1998 | Kammerer et al. | |
| 5,769,870 A | 6/1998 | Salahieh et al. | |
| 5,776,147 A | 7/1998 | Dolendo | |
| 5,776,150 A | 7/1998 | Nolan et al. | |
| 5,779,707 A | 7/1998 | Bertholet et al. | |
| 5,780,807 A | 7/1998 | Saunders | |
| 5,782,844 A | 7/1998 | Yoon et al. | |
| 5,782,860 A | 7/1998 | Epstein et al. | |
| 5,782,861 A | 7/1998 | Cragg et al. | |
| 5,782,864 A | 7/1998 | Lizardi | |
| 5,795,958 A | 8/1998 | Rao et al. | |
| 5,797,928 A | 8/1998 | Kogasaka | |
| 5,797,929 A | 8/1998 | Andreas et al. | |
| 5,797,931 A | 8/1998 | Bito et al. | |
| 5,797,933 A | 8/1998 | Snow et al. | |
| 5,797,958 A | 8/1998 | Yoon | |
| 5,797,960 A | 8/1998 | Stevens et al. | |
| 5,810,776 A | 9/1998 | Bacich et al. | |

(56) References Cited

U.S. PATENT DOCUMENTS

| | | |
|---|---|---|
| 5,810,846 A | 9/1998 | Virnich et al. |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,845,657 A | 12/1998 | Carberry et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | LeVeen et al. |
| 5,858,082 A | 1/1999 | Cruz et al. |
| 5,860,991 A * | 1/1999 | Klein et al. .................. 606/144 |
| 5,861,003 A | 1/1999 | Latson et al. |
| 5,861,005 A | 1/1999 | Kontos |
| 5,868,755 A | 2/1999 | Kanner et al. |
| 5,868,762 A | 2/1999 | Cragg et al. |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,159 A | 11/1999 | Bolduc et al. |
| 5,976,161 A | 11/1999 | Kirsch et al. |
| 5,976,174 A | 11/1999 | Ruiz |
| 5,980,517 A | 11/1999 | Gough et al. |
| 5,984,934 A | 11/1999 | Ashby et al. |
| 5,984,948 A | 11/1999 | Hasson |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |
| 6,045,570 A | 4/2000 | Epstein et al. |
| 6,048,358 A | 4/2000 | Barak |
| 6,056,744 A | 5/2000 | Edwards |
| 6,056,768 A | 5/2000 | Cates et al. |
| 6,056,769 A | 5/2000 | Epstein et al. |
| 6,056,770 A | 5/2000 | Epstein et al. |
| 6,059,800 A | 5/2000 | Hart et al. |
| 6,059,825 A | 5/2000 | Hobbs et al. |
| 6,063,085 A | 5/2000 | Tay et al. |
| 6,063,114 A | 5/2000 | Nash et al. |
| 6,066,160 A | 5/2000 | Colvin et al. |
| 6,068,603 A | 5/2000 | Suzuki |
| 6,071,300 A * | 6/2000 | Brenneman et al. .......... 606/213 |
| 6,074,395 A | 6/2000 | Trott et al. |
| 6,074,409 A | 6/2000 | Goldfarb |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,083,242 A | 7/2000 | Cook |
| 6,086,608 A | 7/2000 | Ek et al. |
| 6,090,130 A | 7/2000 | Nash et al. |
| 6,092,561 A | 7/2000 | Schmid |
| 6,095,155 A | 8/2000 | Criscuolo |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock |
| 6,113,610 A | 9/2000 | Poncet |
| 6,113,612 A | 9/2000 | Swanson et al. |
| 6,117,125 A | 9/2000 | Rothbarth et al. |
| 6,117,148 A | 9/2000 | Ravo |
| 6,117,157 A | 9/2000 | Tekulve |
| 6,117,159 A | 9/2000 | Huebsch et al. |
| 6,120,524 A | 9/2000 | Taheri |
| 6,126,675 A | 10/2000 | Schervinsky et al. |
| 6,126,677 A | 10/2000 | Ganaja et al. |
| 6,136,010 A | 10/2000 | Modesitt et al. |
| 6,143,004 A | 11/2000 | Davis |
| 6,143,017 A | 11/2000 | Thal |
| 6,146,385 A | 11/2000 | Torrie et al. |
| 6,149,660 A | 11/2000 | Laufer et al. |
| 6,149,667 A | 11/2000 | Hovland et al. |
| 6,152,144 A | 11/2000 | Lesh et al. |
| 6,152,934 A | 11/2000 | Harper et al. |
| 6,152,936 A | 11/2000 | Christy et al. |
| 6,152,937 A | 11/2000 | Peterson et al. |
| 6,159,234 A | 12/2000 | Bonutti et al. |
| 6,161,263 A | 12/2000 | Anderson |
| 6,165,204 A | 12/2000 | Levinson et al. |
| 6,171,277 B1 | 1/2001 | Ponzi |
| 6,171,329 B1 | 1/2001 | Shaw et al. |
| 6,174,322 B1 | 1/2001 | Schneidt |
| 6,174,324 B1 | 1/2001 | Egan et al. |
| 6,179,849 B1 | 1/2001 | Yencho et al. |
| 6,179,860 B1 | 1/2001 | Fulton, III et al. |
| 6,193,708 B1 | 2/2001 | Ken et al. |
| 6,193,734 B1 | 2/2001 | Bolduc et al. |
| 6,197,042 B1 | 3/2001 | Ginn et al. |
| 6,198,974 B1 | 3/2001 | Webster, Jr. |
| 6,200,329 B1 | 3/2001 | Fung et al. |
| 6,200,330 B1 | 3/2001 | Benderev et al. |

(56) References Cited

U.S. PATENT DOCUMENTS

| | | |
|---|---|---|
| 6,203,565 B1 | 3/2001 | Bonutti et al. |
| 6,206,895 B1 | 3/2001 | Levinson |
| 6,206,913 B1 | 3/2001 | Yencho et al. |
| 6,206,931 B1 | 3/2001 | Cook et al. |
| 6,210,407 B1 | 4/2001 | Webster |
| 6,220,248 B1 | 4/2001 | Voegele et al. |
| 6,221,084 B1 | 4/2001 | Fleenor |
| 6,221,102 B1 | 4/2001 | Baker et al. |
| 6,231,561 B1 | 5/2001 | Frazier et al. |
| 6,231,592 B1 | 5/2001 | Bonutti et al. |
| 6,238,705 B1 | 5/2001 | Liu et al. |
| 6,241,740 B1 | 6/2001 | Davis et al. |
| 6,245,079 B1 | 6/2001 | Nobles et al. |
| 6,248,124 B1 | 6/2001 | Pedros et al. |
| 6,254,615 B1 | 7/2001 | Bolduc et al. |
| 6,254,617 B1 | 7/2001 | Spence et al. |
| 6,254,642 B1 | 7/2001 | Taylor |
| 6,258,115 B1 | 7/2001 | Dubrul |
| 6,267,773 B1 | 7/2001 | Gadberry et al. |
| 6,273,903 B1 | 8/2001 | Wilk |
| 6,277,140 B2 | 8/2001 | Ginn et al. |
| 6,280,460 B1 | 8/2001 | Bolduc et al. |
| 6,287,322 B1 | 9/2001 | Zhu et al. |
| 6,287,335 B1 | 9/2001 | Drasler et al. |
| 6,290,674 B1 | 9/2001 | Roue et al. |
| 6,296,657 B1 | 10/2001 | Brucker |
| 6,302,870 B1 | 10/2001 | Jacobsen et al. |
| 6,302,898 B1 | 10/2001 | Edwards et al. |
| 6,305,891 B1 | 10/2001 | Burlingame |
| 6,306,081 B1 | 10/2001 | Ishikawa et al. |
| 6,309,416 B1 | 10/2001 | Swanson et al. |
| 6,319,258 B1 | 11/2001 | McAllen, III et al. |
| 6,322,580 B1 | 11/2001 | Kanner |
| 6,328,727 B1 | 12/2001 | Frazier et al. |
| 6,329,386 B1 | 12/2001 | Mollison |
| 6,334,865 B1 | 1/2002 | Redmond et al. |
| 6,348,064 B1 | 2/2002 | Kanner |
| 6,355,052 B1 | 3/2002 | Neuss et al. |
| 6,358,258 B1 | 3/2002 | Arcia et al. |
| 6,375,671 B1 | 4/2002 | Kobayashi et al. |
| D457,958 S | 5/2002 | Dycus |
| 6,383,208 B1 | 5/2002 | Sancoff et al. |
| 6,391,048 B1 | 5/2002 | Ginn et al. |
| 6,395,015 B1 | 5/2002 | Borst et al. |
| 6,397,110 B1 | 5/2002 | Kuzma |
| 6,398,752 B1 | 6/2002 | Sweezer et al. |
| 6,402,765 B1 | 6/2002 | Monassevitch et al. |
| 6,409,739 B1 | 6/2002 | Nobles et al. |
| 6,419,669 B1 | 7/2002 | Frazier et al. |
| 6,421,899 B1 | 7/2002 | Zitnay |
| 6,423,054 B1 | 7/2002 | Ouchi |
| 6,425,911 B1 | 7/2002 | Akerfeldt et al. |
| 6,428,472 B1 | 8/2002 | Haas |
| 6,428,548 B1 | 8/2002 | Durgin et al. |
| 6,443,158 B1 | 9/2002 | Lafontaine et al. |
| 6,443,963 B1 | 9/2002 | Baldwin et al. |
| 6,447,540 B1 | 9/2002 | Fontaine et al. |
| 6,450,391 B1 | 9/2002 | Kayan et al. |
| 6,455,053 B1 | 9/2002 | Okada et al. |
| 6,458,130 B1 | 10/2002 | Frazier et al. |
| 6,461,364 B1 | 10/2002 | Ginn et al. |
| 6,461,366 B1 | 10/2002 | Seguin |
| 6,482,224 B1 | 11/2002 | Michler et al. |
| 6,488,692 B1 | 12/2002 | Spence et al. |
| 6,500,115 B2 | 12/2002 | Krattiger et al. |
| 6,506,210 B1 | 1/2003 | Kanner |
| 6,508,828 B1 | 1/2003 | Akerfeldt et al. |
| 6,514,280 B1 | 2/2003 | Gilson |
| 6,517,498 B1 | 2/2003 | Burbank et al. |
| 6,517,555 B1 | 2/2003 | Caro |
| 6,517,569 B2 | 2/2003 | Mikus et al. |
| 6,527,737 B2 | 3/2003 | Kaneshige |
| 6,533,762 B2 | 3/2003 | Kanner et al. |
| 6,533,812 B2 | 3/2003 | Swanson et al. |
| 6,537,288 B2 | 3/2003 | Vargas et al. |
| 6,547,806 B1 | 4/2003 | Ding |
| 6,551,319 B2 | 4/2003 | Lieberman |
| 6,558,349 B1 | 5/2003 | Kirkman |
| 6,569,159 B1 | 5/2003 | Edwards et al. |
| 6,569,173 B1 | 5/2003 | Blatter et al. |
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,596,013 B2 | 7/2003 | Yang et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,652,538 B2 | 11/2003 | Kayan et al. |
| 6,652,556 B1 | 11/2003 | VanTassel et al. |
| 6,663,633 B1 | 12/2003 | Pierson, III |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,685,707 B2 | 2/2004 | Roman et al. |
| 6,689,051 B2 | 2/2004 | Nakada et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,746,472 B2 | 6/2004 | Frazier et al. |
| 6,749,621 B2 | 6/2004 | Pantages et al. |
| 6,749,622 B2 | 6/2004 | McGuckin et al. |
| 6,752,813 B2 | 6/2004 | Goldfarb et al. |
| 6,755,842 B2 | 6/2004 | Kanner et al. |
| 6,758,855 B2 | 7/2004 | Fulton, III et al. |
| 6,767,356 B2 | 7/2004 | Kanner et al. |
| 6,776,785 B1 | 8/2004 | Yencho et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |

(56) References Cited

U.S. PATENT DOCUMENTS

| | | |
|---|---|---|
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,964,668 B2 | 11/2005 | Modesitt et al. |
| 6,969,391 B1 | 11/2005 | Gazzani |
| 6,969,397 B2 | 11/2005 | Ginn |
| 6,984,238 B2 | 1/2006 | Gifford, III et al. |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,033,379 B2 | 4/2006 | Peterson |
| 7,048,747 B2 | 5/2006 | Arcia et al. |
| 7,060,084 B1 | 6/2006 | Loshakove et al. |
| 7,063,661 B2 | 6/2006 | Okada |
| 7,063,711 B1 | 6/2006 | Loshakove et al. |
| 7,074,232 B2 | 7/2006 | Kanner et al. |
| 7,076,305 B2 | 7/2006 | Imran et al. |
| 7,083,635 B2 | 8/2006 | Ginn |
| 7,087,064 B1 | 8/2006 | Hyde |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,220,268 B2 | 5/2007 | Blatter |
| 7,229,452 B2 | 6/2007 | Kayan |
| 7,261,716 B2 | 8/2007 | Strobel et al. |
| 7,270,672 B1 | 9/2007 | Singer |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Bechman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,431,729 B2 | 10/2008 | Chanduszko |
| 7,445,596 B2 | 11/2008 | Kucklick et al. |
| 7,465,286 B2 | 12/2008 | Patterson et al. |
| 7,507,200 B2 | 3/2009 | Okada |
| 7,533,790 B1 | 5/2009 | Knodel et al. |
| 7,582,103 B2 | 9/2009 | Young et al. |
| 7,582,104 B2 | 9/2009 | Corcoran et al. |
| 7,597,706 B2 | 10/2009 | Kanner et al. |
| 7,618,427 B2 | 11/2009 | Ortiz et al. |
| 7,622,628 B2 | 11/2009 | Bergin et al. |
| 7,645,285 B2 | 1/2010 | Cosgrove et al. |
| D611,144 S | 3/2010 | Reynolds |
| 7,678,135 B2 | 3/2010 | Maahs et al. |
| 7,727,249 B2 | 6/2010 | Rahmani |
| 7,731,655 B2 | 6/2010 | Smith et al. |
| 7,749,249 B2 | 7/2010 | Gelbart et al. |
| 7,780,696 B2 | 8/2010 | Daniel et al. |
| 7,799,042 B2 | 9/2010 | Williamson, IV et al. |
| 7,819,895 B2 | 10/2010 | Ginn et al. |
| 7,875,054 B2 | 1/2011 | LaFontaine |
| 7,931,671 B2 | 4/2011 | Tenerz |
| 7,967,842 B2 | 6/2011 | Bakos |
| 8,103,327 B2 | 1/2012 | Harlev et al. |
| 8,105,352 B2 | 1/2012 | Egnelov |
| 8,226,666 B2 | 7/2012 | Zarbatany et al. |
| 8,409,228 B2 | 4/2013 | Blatter et al. |
| 2001/0007077 A1 | 7/2001 | Ginn et al. |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2001/0053909 A1 | 12/2001 | Nakada |
| 2002/0022822 A1 | 2/2002 | Cragg et al. |
| 2002/0026215 A1 | 2/2002 | Redmond et al. |
| 2002/0026216 A1 | 2/2002 | Grimes |
| 2002/0029050 A1 | 3/2002 | Gifford, III et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0049472 A1 | 4/2002 | Coleman et al. |
| 2002/0058960 A1 | 5/2002 | Hudson et al. |
| 2002/0062104 A1 | 5/2002 | Ashby et al. |
| 2002/0072768 A1 | 6/2002 | Ginn |
| 2002/0077657 A1 | 6/2002 | Ginn et al. |
| 2002/0082641 A1 | 6/2002 | Ginn et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0151963 A1 | 10/2002 | Brown et al. |
| 2002/0183786 A1 | 12/2002 | Girton |
| 2002/0183787 A1 | 12/2002 | Wahr et al. |
| 2002/0188275 A1 | 12/2002 | McGuckin et al. |
| 2002/0188318 A1 | 12/2002 | Carley et al. |
| 2002/0193808 A1 | 12/2002 | Belef et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0018358 A1 | 1/2003 | Saadat |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2003/0208211 A1 | 11/2003 | Kortenbach |
| 2003/0233095 A1 | 12/2003 | Urbanski et al. |
| 2004/0009205 A1 | 1/2004 | Sawhney |
| 2004/0009289 A1 | 1/2004 | Carley et al. |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |

(56) References Cited

U.S. PATENT DOCUMENTS

| | | |
|---|---|---|
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chandusko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143290 A1 | 7/2004 | Brightbill |
| 2004/0143291 A1 | 7/2004 | Corcoran et al. |
| 2004/0153122 A1 | 8/2004 | Palermo |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0203552 A1 | 9/2005 | Laufer et al. |
| 2005/0216057 A1 | 9/2005 | Coleman et al. |
| 2005/0222614 A1 | 10/2005 | Ginn et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0256532 A1 | 11/2005 | Nayak et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0020270 A1 | 1/2006 | Jabba et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0135989 A1 | 6/2006 | Carley et al. |
| 2006/0142784 A1 | 6/2006 | Kontos |
| 2006/0144479 A1 | 7/2006 | Carley et al. |
| 2006/0167484 A1 | 7/2006 | Carley et al. |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerez |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |
| 2006/0287674 A1 | 12/2006 | Ginn et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049967 A1 | 3/2007 | Sibbitt, Jr. et al. |
| 2007/0049968 A1 | 3/2007 | Sibbitt, Jr. et al. |
| 2007/0049970 A1 | 3/2007 | Belef et al. |
| 2007/0060895 A1 | 3/2007 | Sibbitt, Jr. et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0172430 A1 | 7/2007 | Brito et al. |
| 2007/0179527 A1 | 8/2007 | Eskuri et al. |
| 2007/0185530 A1 | 8/2007 | Chin-Chen et al. |
| 2007/0203506 A1 | 8/2007 | Sibbitt, Jr. et al. |
| 2007/0203507 A1 | 8/2007 | McLaughlin et al. |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green, III et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282373 A1 | 12/2007 | Ashby et al. |
| 2008/0004636 A1 | 1/2008 | Walberg |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0210737 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287967 A1 | 11/2008 | Andreas et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312667 A1 | 12/2008 | Drasler et al. |

(56) References Cited

U.S. PATENT DOCUMENTS

| | | |
|---|---|---|
| 2008/0312686 A1 | 12/2008 | Ellingwood |
| 2008/0312740 A1 | 12/2008 | Wachter et al. |
| 2008/0319475 A1 | 12/2008 | Clark |
| 2009/0054912 A1 | 2/2009 | Heanue et al. |
| 2009/0105728 A1 | 4/2009 | Noda et al. |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0254119 A1 | 10/2009 | Sibbitt, Jr. et al. |
| 2009/0287244 A1 | 11/2009 | Kokish |
| 2009/0312789 A1 | 12/2009 | Kassab et al. |
| 2010/0042144 A1 | 2/2010 | Bennett |
| 2010/0114156 A1 | 5/2010 | Mehl |
| 2010/0114159 A1 | 5/2010 | Roorda et al. |
| 2010/0130965 A1 | 5/2010 | Sibbitt, Jr. et al. |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0249828 A1 | 9/2010 | Mavani et al. |
| 2011/0066163 A1 | 3/2011 | Cho et al. |
| 2011/0082495 A1 | 4/2011 | Ruiz |
| 2011/0178548 A1 | 7/2011 | Tenerz |
| 2011/0270282 A1 | 11/2011 | Lemke |
| 2012/0035630 A1 | 2/2012 | Roorda |
| 2012/0101520 A1 | 4/2012 | Ginn et al. |
| 2012/0245603 A1 | 9/2012 | Voss |
| 2012/0245623 A1 | 9/2012 | Kariniemi et al. |
| 2012/0245626 A1 | 9/2012 | Ellingwood et al. |
| 2012/0310261 A1 | 12/2012 | Cummins et al. |
| 2013/0006274 A1 | 1/2013 | Walberg et al. |
| 2013/0338708 A1 | 12/2013 | Cummins et al. |
| 2014/0142624 A1 | 5/2014 | Pantages et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |

FOREIGN PATENT DOCUMENTS

| | | |
|---|---|---|
| DE | 197 11 288 | 10/1998 |
| DE | 29723736U 1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 621 032 | 10/1994 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 11500642 | 8/1997 |
| JP | 2000102546 | 4/2000 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/40849 | 8/1999 |
| WO | WO 99/60941 | 12/1999 |
| WO | WO 99/62408 | 12/1999 |
| WO | WO 99/62415 | 12/1999 |
| WO | 00/07505 | 2/2000 |
| WO | WO 00/06029 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |

(56) References Cited

FOREIGN PATENT DOCUMENTS

| | | |
|---|---|---|
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150915 | 12/2008 |
| WO | WO 2009/079091 | 6/2009 |
| WO | WO 2010/031050 | 3/2010 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 10/264,306, Oct. 4, 2005, Office Action.
U.S. Appl. No. 10/264,306, May 10, 2006, Notice of Allowance.
U.S. Appl. No. 10/264,306, Jul. 2, 2007, Notice of Allowance.
U.S. Appl. No. 10/264,306, Feb. 4, 2008, Notice of Allowance.
U.S. Appl. No. 10/264,306, Jun. 27, 2008, Office Action.
U.S. Appl. No. 10/305,923, Nov. 1, 2004, Office Action.
U.S. Appl. No. 10/305,923, Mar. 3, 2005, Notice of Allowance.
U.S. Appl. No. 10/335,075, Aug. 10, 2005, Office Action.
U.S. Appl. No. 10/335,075, Dec. 19, 2005, Office Action.
U.S. Appl. No. 10/335,075, Apr. 21, 2006, Office Action.
U.S. Appl. No. 10/335,075, Dec. 27, 2006, Notice of Allowance.
U.S. Appl. No. 10/335,075, Apr. 11, 2007, Issue Notification.
U.S. Appl. No. 10/356,214, Nov. 30, 2005, Office Action.
U.S. Appl. No. 10/356,214, Aug. 23, 2006, Office Action.
U.S. Appl. No. 10/356,214, Feb. 13, 2007, Office Action.
U.S. Appl. No. 10/356,214, Sep. 12, 2007, Office Action.
U.S. Appl. No. 10/356,214, Mar. 6, 2008, Office Action.
U.S. Appl. No. 10/356,214, Nov. 4, 2008, Office Action.
U.S. Appl. No. 10/435,104, Jun. 10, 2004, Office Action.
U.S. Appl. No. 10/435,104, Sep. 21, 2004, Notice of Allowance.
U.S. Appl. No. 10/435,104, Jan. 3, 2006, Examiner's Amendment.
U.S. Appl. No. 10/435,104, May 16, 2006, Office Action.
U.S. Appl. No. 10/435,104, Dec. 28, 2006, Notice of Allowance.
U.S. Appl. No. 10/435,104, May 23, 2007, Issue Notification.
U.S. Appl. No. 10/435,104, Jul. 10, 2007, Notice of Allowance.
U.S. Appl. No. 10/435,104, Aug. 2, 2007, Notice of Allowance.
U.S. Appl. No. 10/435,104, Oct. 26, 2007, Notice of Allowance.
U.S. Appl. No. 10/435,104, Nov. 14, 2007, Notice of Allowance.
U.S. Appl. No. 10/435,104, Apr. 4, 2008, Notice of Allowance.
U.S. Appl. No. 10/435,104, Sep. 26, 2008, Notice of Allowance.
U.S. Appl. No. 10/455,768, Nov. 16, 2004, Office Action.
U.S. Appl. No. 10/455,768, Apr. 6, 2005, Notice of Allowance.
U.S. Appl. No. 11/461,323, May 2, 2007, Office Action.
U.S. Appl. No. 11/461,323, Oct. 29, 2007, Office Action.
U.S. Appl. No. 11/461,323, Apr. 25, 2008, Office Action.
U.S. Appl. No. 11/461,323, Nov. 6, 2008, Office Action.
U.S. Appl. No. 10/486,067, Jan. 10, 2006, Office Action.
U.S. Appl. No. 10/486,067, Sep. 20, 2006, Notice of Allowance.
U.S. Appl. No. 10/486,070, Apr. 20, 2005, Office Action.
U.S. Appl. No. 10/486,070, Aug. 10, 2005, Office Action.
U.S. Appl. No. 10/486,070, Oct. 18, 2005, Notice of Allowance.
U.S. Appl. No. 10/517,004, Aug. 13, 2007, Office Action.
U.S. Appl. No. 10/517,004, Jan. 30, 2008, Office Action.
U.S. Appl. No. 10/517,004, Aug. 13, 2008, Notice of Allowance.
U.S. Appl. No. 10/519,778, Feb. 23, 2006, Office Action.
U.S. Appl. No. 10/519,778, May 31, 2006, Notice of Allowance.
U.S. Appl. No. 10/541,083, Oct. 16, 2007, Office Action.
U.S. Appl. No. 10/541,083, Oct. 31, 2007, Office Action.
U.S. Appl. No. 10/541,083, May 5, 2008, Office Action.
U.S. Appl. No. 10/541,083, Sep. 19, 2008, Notice of Allowance.
U.S. Appl. No. 10/616,832, Jun. 30, 2006, Office Action.
U.S. Appl. No. 10/616,832, Oct. 20, 2006, Office Action.
U.S. Appl. No. 10/616,832, May 29, 2007, Office Action.
U.S. Appl. No. 10/616,832, Jan. 22, 2008, Office Action.
U.S. Appl. No. 10/616,832, Sep. 17, 2008, Office Action.
U.S. Appl. No. 10/617,090, Mar. 22, 2005, Office Action.
U.S. Appl. No. 10/617,090, Jul. 6, 2005, Notice of Allowance.
U.S. Appl. No. 10/617,090, Oct. 5, 2005, Notice of Allowance.
U.S. Appl. No. 10/638,115, Sep. 22, 2006, Office Action.
U.S. Appl. No. 10/638,115, Jan. 31, 2007, Office Action.
U.S. Appl. No. 10/638,115, Sep. 18, 2007, Office Action.
U.S. Appl. No. 10/638,115, Feb. 7, 2008, Office Action.
U.S. Appl. No. 10/638,115, Oct. 29, 2008, Office Action.
U.S. Appl. No. 10/667,144, Sep. 19, 2006, Office Action.
U.S. Appl. No. 10/667,144, May 2, 2007, Office Action.
U.S. Appl. No. 10/667,144, Nov. 19, 2007, Office Action.
U.S. Appl. No. 10/667,144, Dec. 5, 2007, Office Action.
U.S. Appl. No. 10/667,144, May 12, 2008, Office Action.
U.S. Appl. No. 10/682,459, Sep. 15, 2006, Office Action.
U.S. Appl. No. 10/682,459, Apr. 18, 2007, Office Action.
U.S. Appl. No. 10/682,459, Apr. 2, 2008, Office Action.
U.S. Appl. No. 10/786,444, Oct. 30, 2006, Office Action.
U.S. Appl. No. 10/786,444, Apr. 17, 2007, Office Action.
U.S. Appl. No. 10/786,444, Aug. 31, 2007, Office Action.
U.S. Appl. No. 10/786,444, Apr. 24, 2008, Office Action.
U.S. Appl. No. 10/786,444, Oct. 17, 2008, Office Action.
U.S. Appl. No. 10/787,073, Nov. 30, 2006, Office Action.
U.S. Appl. No. 10/787,073, Sep. 5, 2007, Office Action.
U.S. Appl. No. 10/787,073, Feb. 22, 2008, Office Action.
U.S. Appl. No. 10/787,073, Nov. 12, 2008, Office Action.
U.S. Appl. No. 10/908,721, Oct. 19, 2006, Office Action.
U.S. Appl. No. 10/908,721, Aug. 10, 2007, Office Action.
U.S. Appl. No. 10/908,721, Jan. 25, 2008, Office Action.
U.S. Appl. No. 10/908,721, Nov. 25, 2008, Office Action.
U.S. Appl. No. 11/113,549, Feb. 6, 2007, Office Action.
U.S. Appl. No. 11/113,549, May 30, 2007, Office Action.
U.S. Appl. No. 11/113,549, Nov. 9, 2007, Office Action.
U.S. Appl. No. 11/113,549, Apr. 16, 2008, Office Action.
U.S. Appl. No. 11/152,562, May 13, 2008, Office Action.
U.S. Appl. No. 11/198,811, Aug. 26, 2008, Office Action.
U.S. Appl. No. 11/344,891, Apr. 29, 2008, Office Action.
U.S. Appl. No. 11/406,203, May 14, 2007, Office Action.
U.S. Appl. No. 11/406,203, Jan. 29, 2008, Notice of Allowance.
U.S. Appl. No. 11/406,203, May 23, 2008, Notice of Allowance.
U.S. Appl. No. 11/406,203, Sep. 22, 2008, Notice of Allowance.
U.S. Appl. No. 11/411,925, Jun. 6, 2007, Office Action.
U.S. Appl. No. 11/411,925, Feb. 5, 2008, Office Action.
U.S. Appl. No. 11/744,089, Nov. 26, 2008, Office Action.
U.S. Appl. No. 60/696,069, Jul. 1, 2005, Pantages et al.
U.S. Appl. No. 60/946,026, Jun. 25, 2007, Ellingwood.
U.S. Appl. No. 12/393,877, Feb. 26, 2009, Ellingwood et al.
U.S. Appl. No. 12/402,398, Mar. 11, 2009, Carley et al.
U.S. Appl. No. 12/403,256, Mar. 12, 2009, Carley et al.
U.S. Appl. No. 12/403,277, Mar. 12, 2009, Coleman et al.

(56) References Cited

OTHER PUBLICATIONS

U.S. Appl. No. 09/610,238, May 3, 2002, Issue Notification.
U.S. Appl. No. 09/680,837, Jul. 9, 2002, Office Action.
U.S. Appl. No. 09/680,837, Nov. 6, 2002, Office Action.
U.S. Appl. No. 09/680,837, Mar. 25, 2003, Office Action.
U.S. Appl. No. 09/680,837, Jun. 16, 2003, Notice of Allowance.
U.S. Appl. No. 09/680,837, Sep. 11, 2003, Issue Notification.
U.S. Appl. No. 10/006,400, Jan. 2, 2009, Office Action.
U.S. Appl. No. 10/081,726, Sep. 4, 2003, Issue Notification.
U.S. Appl. No. 10/147,774, Mar. 18, 2009, Office Action.
U.S. Appl. No. 10/264,306, Feb. 26, 2009, Office Action.
U.S. Appl. No. 10/356,214, Apr. 29, 2009, Office Action.
U.S. Appl. No. 10/435,104, Feb. 15, 2006, Issue Notification.
U.S. Appl. No. 10/435,104, Dec. 22, 2008, Notice of Allowance.
U.S. Appl. No. 10/486,067, Dec. 27, 2006, Issue Notification.
U.S. Appl. No. 10/517,004, Feb. 10, 2009, Notice of Allowance.
U.S. Appl. No. 10/541,083, Dec. 29, 2008, Notice of Allowance.
U.S. Appl. No. 10/541,083, Apr. 16, 2009, Notice of Allowance.
U.S. Appl. No. 10/617,090, Feb. 1, 2006, Issue Notification.
U.S. Appl. No. 10/638,115, May 7, 2009, Notice of Allowance.
U.S. Appl. No. 10/667,144, Mar. 24, 2009, Office Action.
U.S. Appl. No. 10/669,313, Jan. 11, 2006, Notice of Allowance.
U.S. Appl. No. 10/669,313, Jun. 28, 2006, Notice of Allowance.
U.S. Appl. No. 10/669,313, Nov. 15, 2006, Issue Notification.
U.S. Appl. No. 10/682,459, Dec. 4, 2008, Office Action.
U.S. Appl. No. 10/682,459, Jun. 10, 2009, Office Action.
U.S. Appl. No. 11/048,503, Mar. 13, 2009, Office Action.
U.S. Appl. No. 11/152,562, Feb. 13, 2009, Office Action.
U.S. Appl. No. 11/344,793, Jan. 22, 2009, Office Action.
U.S. Appl. No. 11/344,868, Mar. 25, 2009, Office Action.
U.S. Appl. No. 11/344,891, Dec. 8, 2008, Office Action.
U.S. Appl. No. 11/344,891, Feb. 26, 2009, Office Action.
U.S. Appl. No. 11/390,586, Jun. 24, 2009, Office Action.
U.S. Appl. No. 11/396,141, May 22, 2009, Office Action.
U.S. Appl. No. 11/396,731, Feb. 13, 2009, Office Action.
U.S. Appl. No. 11/396,731, May 22, 2009, Office Action.
U.S. Appl. No. 11/406,203, Mar. 3, 2009, Office Action.
U.S. Appl. No. 11/411,925, Jan. 12, 2009, Office Action.
U.S. Appl. No. 11/427,297, Jan. 30, 2009, Office Action.
U.S. Appl. No. 11/532,325, Feb. 23, 2009, Office Action.
U.S. Appl. No. 11/532,325, Jun. 17, 2009, Office Action.
U.S. Appl. No. 12/106,928, Jan. 23, 2009, Office Action.
U.S. Appl. No. 12/481,377, Jan. 3, 2012, Office Action.
U.S. Appl. No. 12/548,274, Dec. 28, 2011, Office Action.
U.S. Appl. No. 12/684,562, Dec. 28, 2011, Office Action.
U.S. Appl. No. 11/113,549, Jan. 4, 2011, Office Action
U.S. Appl. No. 12/941,809, Nov. 8, 2010, Ginn et al.
U.S. Appl. No. 12/950,628, Nov. 19, 2010, Walberg et al.
U.S. Appl. No. 12/955,859, Nov. 29, 2010, Ginn.
U.S. Appl. No. 12/945,646, Nov. 12, 2010, Carley et al.
U.S. Appl. No. 12/973,204, Dec. 20, 2010, Jabba et al.
U.S. Appl. No. 12/987,792, Jan. 10, 2011, Palermo et al.
U.S. Appl. No. 12/608,773, Jan. 7, 2013, Office Action.
U.S. Appl. No. 13/490,143, Jan. 4, 2013, Restriction Requirement.
U.S. Appl. No. 13/615,547, Jan. 18, 2013, Office Action.
U.S. Appl. No. 12/897,358, Jan. 12, 2012, Notice of Allowance.
U.S. Appl. No. 10/435,104, Jan. 12, 2011, Issue Notification.
U.S. Appl. No. 12/338,977, Jan. 19, 2012, Office Action.
U.S. Appl. No. 12/684,569, Jan. 27, 2012, Office Action.
U.S. Appl. No. 11/344,891, Jan. 22, 2013, Notice of Allowance.
U.S. Appl. No. 13/030,922, Jan. 31, 2013, Office Action.
U.S. Appl. No. 13/153,594, Jan. 29, 2013, Office Action.
U.S. Appl. No. 10/616,832, Jan. 26, 2011, Issue Notification.
U.S. Appl. No. 11/152,562, Jan. 26, 2011, Issue Notification.
U.S. Appl. No. 11/767,818, Feb. 3, 2012, Notice of Allowance.
U.S. Appl. No. 12/684,542, Jan. 30, 2012, Office Action.
U.S. Appl. No. 12/941,809, Jan. 30, 2012, Office Action.
U.S. Appl. No. 12/966,923, Feb. 3, 2012, Notice of Allowance.
U.S. Appl. No. 12/961,331, Feb. 1, 2013, Office Action.
U.S. Appl. No. 13/488,233, Feb. 5, 2013, Notice of Allowance.
U.S. Appl. No. 12/608,769, Feb. 10, 2012, Office Action.
U.S. Appl. No. 12/684,400, Feb. 13, 2012, Office Action.
U.S. Appl. No. 12/724,304, Feb. 10, 2012, Office Action.
U.S. Appl. No. 60/693,531, Jun. 24, 2005, Carley.
Marshall A.C., Lock J.E., Structural and Compliant Anatomy of the Patent Foramen Ovale in Patients Undergoing Transcatheter Closure, Am Heart J Aug. 2000; 140(2); pp. 303-7.
Taber's Cyclopedic Medical Dictionary, 18th Ed. 1997, pp. 747 and 1420.
U.S. Appl. No. 10/006,400, Jul. 9, 2009, Notice of Allowance.
U.S. Appl. No. 10/006,400, Jan. 13, 2010, Notice of Allowance.
U.S. Appl. No. 10/147,774, Oct. 26, 2009, Office Action.
U.S. Appl. No. 10/264,306, Aug. 13, 2009, Office Action.
U.S. Appl. No. 10/356,214, Jan. 13, 2010, Notice of Allowance.
U.S. Appl. No. 10/435,104, Jan. 20, 2010, Notice of Allowance.
U.S. Appl. No. 10/517,004, Jun. 26, 2009, Notice of Allowance.
U.S. Appl. No. 10/517,004, Jan. 11, 2010, Notice of Allowance.
U.S. Appl. No. 10/616,832, Jan. 11, 2010, Notice of Allowance.
U.S. Appl. No. 10/541,083, Sep. 30, 2009, Notice of Allowance.
U.S. Appl. No. 10/616,832, Jul. 21, 2009, Office Action.
U.S. Appl. No. 10/667,144, Nov. 23, 2009, Office Action.
U.S. Appl. No. 10/682,459, Dec. 23, 2009, Office Action.
U.S. Appl. No. 10/786,444, Jun. 18, 2009, Office Action.
U.S. Appl. No. 10/786,444, Jan. 14, 2010, Office Action.
U.S. Appl. No. 10/787,073, Aug. 13, 2009, Office Action.
U.S. Appl. No. 10/908,721, Jun. 23, 2009, Office Action.
U.S. Appl. No. 11/048,503, Jun. 26, 2009, Office Action.
U.S. Appl. No. 11/048,503, Jan. 11, 2010, Notice of Allowance.
U.S. Appl. No. 11/113,549, Jul. 21, 2009, Office Action.
U.S. Appl. No. 11/152,562, Jul. 6, 2009, Office Action.
U.S. Appl. No. 11/198,811, Sep. 22, 2009, Office Action.
U.S. Appl. No. 11/344,891, Oct. 7, 2009, Office Action.
U.S. Appl. No. 11/396,141, Aug. 26, 2009, Office Action.
U.S. Appl. No. 11/406,203, Sep. 16, 2009, Office Action.
U.S. Appl. No. 11/411,925, Sep. 10, 2009, Office Action.
U.S. Appl. No. 11/427,297, Sep. 15, 2009, Office Action.
U.S. Appl. No. 11/455,993, Feb. 17, 2009, Office Action.
U.S. Appl. No. 11/455,993, Dec. 16, 2009, Office Action.
U.S. Appl. No. 11/461,323, Jul. 27, 2009, Office Action.
U.S. Appl. No. 11/532,325, Jan. 5, 2010, Office Action.
U.S. Appl. No. 11/675,462, Dec. 10, 2009, Office Action.
U.S. Appl. No. 11/744,089, Aug. 14, 2009, Office Action.
U.S. Appl. No. 11/958,295, Aug. 27, 2009, Office Action.
U.S. Appl. No. 11/959,334, Aug. 19, 2009, Office Action.
U.S. Appl. No. 11/959,334, Jan. 12, 2010, Notice of Allowance.
U.S. Appl. No. 12/106,928, Oct. 5, 2009, Office Action.
U.S. Appl. No. 12/403,256, Dec. 16, 2009, Office Action.
U.S. Appl. No. 13/017,636, filed Jan. 31, 2011, Carley et al.
U.S. Appl. No. 13/026,989, filed Feb. 14, 2011, Cummins.
U.S. Appl. No. 10/264,306, Feb. 16, 2011, Issue Notification.
U.S. Appl. No. 11/767,818, Feb. 16, 2011, Office Action.
U.S. Appl. No. 10/667,144, Feb. 15, 2012, Issue Notification.
U.S. Appl. No. 12/135,858, Feb. 16, 2012, Office Action.
U.S. Appl. No. 12/684,562, Feb. 16, 2012, Office Action.
U.S. Appl. No. 12/945,646, Feb. 21, 2012, Notice of Allowance.
U.S. Appl. No. 12/143,020, Feb. 23, 2012, Notice of Allowance.
U.S. Appl. No. 12/548,274, Mar. 2, 2012, Office Action.
U.S. Appl. No. 12/642,319, Feb. 27, 2012, Office Action.
U.S. Appl. No. 11/852,190, Mar. 2, 2011, Office Action.
U.S. Appl. No. 12/122,603, Mar. 3, 2011, Office Action.
U.S. Appl. No. 11/958,281, Mar. 10, 2011, Office Action.
U.S. Appl. No. 11/532,576, Mar. 16, 2011, Issue Notification.
U.S. Appl. No. 12/114,031, Mar. 6, 2012, Office Action.
U.S. Appl. No. 12/684,470, Mar. 23, 2012, Office Action.
U.S. Appl. No. 12/688,065, Mar. 13, 2012, Office Action.
U.S. Appl. No. 12/897,358, Mar. 5, 2012, Notice of Allowance.
U.S. Appl. No. 12/973,204, Mar. 7, 2012, Notice of Allowance.
U.S. Appl. No. 12/987,792, Mar. 13, 2012, Office Action.
U.S. Appl. No. 11/396,731, Mar. 22, 2011, Office Action.
U.S. Appl. No. 11/427,297, Mar. 21, 2011, Office Action.
U.S. Appl. No. 12/113,851, Mar. 29, 2012, Office Action.
U.S. Appl. No. 12/403,277, Apr. 3, 2012, Office Action.
U.S. Appl. No. 10/682,459, Apr. 1, 2011, Notice of Allowance.

(56) References Cited

OTHER PUBLICATIONS

U.S. Appl. No. 12/403,277, Mar. 31, 2011, Office Action.
U.S. Appl. No. 13/791,829, filed Mar. 8, 2013, Roorda et al.
U.S. Appl. No. 13/791,846, filed Mar. 8, 2013, Palermo.
U.S. Appl. No. 13/112,618, Mar. 29, 2013, Office Action.
U.S. Appl. No. 13/112,631, Mar. 29, 2013, Office Action.
U.S. Appl. No. 13/308,227, Apr. 10, 2013, Office Action.
U.S. Appl. No. 13/525,839, Apr. 1, 2013, Office Action.
U.S. Appl. No. 10/147,774, Apr. 6, 2011, Issue Notification.
U.S. Appl. No. 12/114,091, Apr. 5, 2012, Office Action.
U.S. Appl. No. 12/684,542, Apr. 16, 2012, Office Action.
U.S. Appl. No. 11/744,089, Apr. 15, 2013, Office Action.
U.S. Appl. No. 12/850,242, Apr. 18, 2013, Office Action.
U.S. Appl. No. 13/052,634, Feb. 8, 2013, Office Action.
U.S. Appl. No. 13/052,634, Apr. 22, 2013, Office Action.
U.S. Appl. No. 13/615,547, Apr. 12, 2013, Notice of Allowance.
U.S. Appl. No. 12/122,603, Apr. 22, 2011, Office Action.
U.S. Appl. No. 13/308,227, filed Nov. 30, 2011, Yibarren.
U.S. Appl. No. 12/688,065, Apr. 26, 2012, Office Action.
U.S. Appl. No. 11/396,141, Apr. 30, 2013, Office Action.
U.S. Appl. No. 11/852,190, Apr. 24, 2013, Office Action.
U.S. Appl. No. 12/848,642, Apr. 26, 2013, Office Action.
U.S. Appl. No. 13/490,143, Apr. 29, 2013, Notice of Allowance.
U.S. Appl. No. 12/113,851, Apr. 27, 2011, Office Action.
U.S. Appl. No. 12/481,377, Apr. 28, 2011, Office Action.
U.S. Appl. No. 12/114,031, May 11, 2011, Office Action.
U.S. Appl. No. 12/143,020, May 11, 2011, Office Action.
U.S. Appl. No. 11/344,891, May 15, 2013, Issue Notification.
U.S. Appl. No. 12/955,859, May 16, 2013, Office Action.
U.S. Appl. No. 13/488,233, May 15, 2013, Issue Notification.
U.S. Appl. No. 11/390,586, May 3, 2012, Notice of Allowance.
U.S. Appl. No. 12/684,400, May 9, 2012, Office Action.
U.S. Appl. No. 12/897,358, May 2, 2012, Issue Notification.
U.S. Appl. No. 12/966,923, May 16, 2012, Issue Notification.
U.S. Appl. No. 12/143,020, May 30, 2012, Issue Notification.
U.S. Appl. No. 12/393,877, May 21, 2012, Office Action.
U.S. Appl. No. 12/941,809, Jun. 1, 2012, Office Action.
U.S. Appl. No. 12/945,646, May 30, 2012, Issue Notification.
U.S. Appl. No. 12/973,205, May 30, 2012, Issue Notification.
U.S. Appl. No. 13/028,041, filed Feb. 15, 2011, Von Oepen.
U.S. Appl. No. 13/112,618, filed May 20, 2011, Gianotti et al.
U.S. Appl. No. 13/112,631, filed May 20, 2011, Voss.
U.S. Appl. No. 12/955,859, May 26, 2011, Office Action.
U.S. Appl. No. 13/153,594, filed Jun. 6, 2011, Reyes et al.
U.S. Appl. No. 10/667,144, Jun. 6, 2011, Office Action.
U.S. Appl. No. 12/608,773, Jun. 7, 2012, Office Action.
U.S. Appl. No. 13/026,989, Jun. 8, 2012, Office Action.
U.S. Appl. No. 12/481,377, Jun. 21, 2011, Office Action.
U.S. Appl. No. 12/114,091, Jul. 7, 2011, Office Action.
U.S. Appl. No. 12/945,646, Jul. 6, 2011, Office Action.
U.S. Appl. No. 13/525,839, filed Jun. 18, 2012, Carley et al.
U.S. Appl. No. 11/427,297, Jun. 26, 2012, Notice of Allowance.
U.S. Appl. No. 11/767,818, Jul. 4, 2012, Issue Notification.
U.S. Appl. No. 12/338,977, Jul. 11, 2012, Office Action.
U.S. Appl. No. 60/711,279, filed Aug. 24, 2005, Sibbitt Jr. et al.
U.S. Appl. No. 60/726,985, filed Oct. 14, 2005, Sibbitt Jr. et al.
U.S. Appl. No. 60/793,444, filed Apr. 20, 2006 Jones et al.
U.S. Appl. No. 61/097,072, Sep. 15, 2008, Sibbitt Jr. et al.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 10/006,400, Apr. 27, 2010, Notice of Allowance.
U.S. Appl. No. 10/147,774, Jun. 8, 2010, Office Action.
U.S. Appl. No. 10/264,306, Jan. 27, 2010, Office Action.
U.S. Appl. No. 10/264,306, Jun. 15, 2010, Office Action.
U.S. Appl. No. 10/356,214, May 13, 2010, Notice of Allowance.
U.S. Appl. No. 10/435,104, Jun. 2, 2010, Office Action.
U.S. Appl. No. 10/517,004, Apr. 23, 2010, Notice of Allowance.
U.S. Appl. No. 10/541,083, Feb. 5, 2010, Notice of Allowance.
U.S. Appl. No. 10/541,083, May 10, 2010, Notice of Allowance.
U.S. Appl. No. 10/616,832, May 12, 2010, Notice of Allowance.
U.S. Appl. No. 10/638,115, Dec. 1, 2009, Notice of Allowance.
U.S. Appl. No. 10/638,115, Apr. 2, 2010, Notice of Allowance.
U.S. Appl. No. 10/667,144, Jun. 22, 2010, Office Action.
U.S. Appl. No. 10/682,459, Apr. 28, 2010, Office Action.
U.S. Appl. No. 10/787,073, Feb. 17, 2010, Notice of Allowance.
U.S. Appl. No. 10/908,721, Feb. 2, 2010, Office Action.
U.S. Appl. No. 11/048,503, Apr. 26, 2010, Notice of Allowance.
U.S. Appl. No. 11/152,562, Mar. 31, 2010, Office Action.
U.S. Appl. No. 11/198,811, Jun. 29, 2010, Notice of Allowance.
U.S. Appl. No. 11/316,775, Apr. 16, 2008, Office Action.
U.S. Appl. No. 11/316,775, Aug. 6, 2008, Office Action.
U.S. Appl. No. 11/344,891, May 7, 2010, Office Action.
U.S. Appl. No. 11/390,586, Jul. 6, 2010, Office Action.
U.S. Appl. No. 11/396,141, May 4, 2010, Office Action.
U.S. Appl. No. 11/396,731, Jun. 29, 2010, Office Action.
U.S. Appl. No. 11/406,203, Jun. 18, 2010, Notice of Allowance.
U.S. Appl. No. 11/508,656, Dec. 9, 2009, Office Action.
U.S. Appl. No. 11/508,656, Mar. 25, 2010, Office Action.
U.S. Appl. No. 11/508,662, Dec. 28, 2009, Office Action.
U.S. Appl. No. 11/508,662, Apr. 14, 2010, Office Action.
U.S. Appl. No. 11/508,715, Jan. 6, 2010, Office Action.
U.S. Appl. No. 11/508,715, Apr. 26, 2010, Office Action.
U.S. Appl. No. 11/532,576, Mar. 1, 2010, Office Action.
U.S. Appl. No. 11/532,576, Apr. 23, 2010, Office Action.
U.S. Appl. No. 11/674,930, Jan. 8, 2009, Office Action.
U.S. Appl. No. 11/674,930, Jun. 4, 2009, Office Action.
U.S. Appl. No. 11/674,930, Jan. 8, 2010, Office Action.
U.S. Appl. No. 11/767,818, Dec. 24, 2009, Office Action.
U.S. Appl. No. 11/767,818, Mar. 22, 2010, Office Action.
U.S. Appl. No. 11/852,190, Jun. 24, 2010, Office Action.
U.S. Appl. No. 11/958,295, May 25, 2010, Office Action.
U.S. Appl. No. 11/959,334, Apr. 14, 2010, Notice of Allowance.
U.S. Appl. No. 12/106,928, May 10, 2010, Office Action.
U.S. Appl. No. 12/113,851, Apr. 27, 2010, Office Action.
U.S. Appl. No. 12/113,851, Jun. 24, 2010, Office Action.
U.S. Appl. No. 12/402,398, Mar. 9, 2010, Office Action.
U.S. Appl. No. 12/402,398, May 20, 2010, Office Action.
U.S. Appl. No. 12/403,256, Mar. 30, 2010, Office Action.
U.S. Appl. No. 29/296,370, Aug. 18, 2008, Office Action.
U.S. Appl. No. 29/296,370, Dec. 2, 2008, Notice of Allowance.
U.S. Appl. No. 29/296,370, Apr. 1, 2009, Notice of Allowance.
U.S. Appl. No. 29/296,370, Feb. 10, 2010, Issue Notification.
U.S. Appl. No. 12/135,858, Jul. 13, 2011, Office Action.
U.S. Appl. No. 11/959,334, Jul. 23, 2010, Notice of Allowance.
U.S. Appl. No. 12/955,859, Jul. 21, 2011, Office Action.
U.S. Appl. No. 11/390,586, Jul. 18, 2012, Issue Notification.
U.S. Appl. No. 12/608,773, Jul. 20, 2012, Office Action.
U.S. Appl. No. 12/684,569, Jul. 30, 2012, Office Action.
U.S. Appl. No. 13/039,087, Jul. 17, 2012, Office Action.
U.S. Appl. No. 11/675,462, Aug. 3, 2011, Office Action.
U.S. Appl. No. 12/114,031, Aug. 2, 2011, Office Action.
U.S. Appl. No. 10/682,459, Aug. 10, 2011, Issue Notification.
U.S. Appl. No. 11/675,462, Aug. 16, 2012, Issue Notification.
U.S. Appl. No. 11/744,089, Aug. 8, 2012, Office Action.
U.S. Appl. No. 12/481,377, Aug. 10, 2012, Notice of Allowance.
U.S. Appl. No. 12/850,242, Aug. 6, 2012, Office Action.
U.S. Appl. No. 12/955,859, Aug. 6, 2012, Office Action.
U.S. Appl. No. 12/608,769, Aug. 22, 2012, Office Action.
U.S. Appl. No. 12/642,319, Aug. 28, 2012, Office Action.
U.S. Appl. No. 12/684,562, Aug. 21, 2012, Office Action.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
U.S. Appl. No. 09/610,128, filed Jul. 5, 2000, Kerievsky.
U.S. Appl. No. 12/548,274, filed Aug. 26, 2008, Clark.
U.S. Appl. No. 12/724,304, filed Mar. 15, 2010, Forston.
U.S. Appl. No. 12/848,642, filed Aug. 2, 2010, Fortson et al.
U.S. Appl. No. 10/006,400, Aug. 2, 2010, Notice of Allowance.
U.S. Appl. No. 10/517,004, Aug. 3, 2010, Notice of Allowance.

(56) References Cited

OTHER PUBLICATIONS

U.S. Appl. No. 10/541,083, Aug. 17, 2010, Notice of Allowance.
U.S. Appl. No. 11/048,503, Jul. 30, 2010, Notice of Allowance.
U.S. Appl. No. 11/427,309, May 28, 2008, Office Action.
U.S. Appl. No. 11/427,309, Jan. 2, 2009, Office Action.
U.S. Appl. No. 11/427,309, Apr. 20, 2009, Office Action.
U.S. Appl. No. 11/427,309, Nov. 6, 2009, Office Action.
U.S. Appl. No. 11/427,309, Apr. 26, 2010, Office Action.
U.S. Appl. No. 11/757,108, Nov. 25, 2009, Office Action.
U.S. Appl. No. 13/222,899, filed Aug. 31, 2011, Carley et al.
U.S. Appl. No. 12/143,020, Aug. 31, 2011, Office Action.
U.S. Appl. No. 12/897,358, Aug. 22, 2011, Office Action.
U.S. Appl. No. 11/396,731, Sep. 1, 2011, Office Action.
U.S. Appl. No. 12/548,274, Sep. 10, 2012, Office Action.
U.S. Appl. No. 12/684,470, Aug. 30, 2012, Office Action.
U.S. Appl. No. 12/684,542, Sep. 13, 2012, Office Action.
U.S. Appl. No. 09/866,551, filed May 25, 2001, Ginn.
U.S. Appl. No. 10/638,115, Aug. 13, 2010, Notice of Allowance.
U.S. Appl. No. 10/787,073, Aug. 25, 2010, Notice of Allowance.
U.S. Appl. No. 11/508,656, Aug. 30, 2010, Office Action.
U.S. Appl. No. 11/675,462, Aug. 31, 2010, Office Action.
U.S. Appl. No. 11/958,281, Sep. 2, 2010, Office Action.
U.S. Appl. No. 12/403,256, Aug. 19, 2010, Notice of Allowance.
U.S. Appl. No. 13/026,989, Sep. 16, 2011, Office Action.
U.S. Appl. No. 12/402,398, Sep. 20, 2012, Office Action.
U.S. Appl. No. 12/688,065, Oct. 12, 2012, Office Action.
U.S. Appl. No. 12/848,642, Sep. 20, 2012, Office Action.
U.S. Appl. No. 12/987,792, Sep. 17, 2012, Office Action.
U.S. Appl. No. 10/616,832, Sep. 20, 2010, Notice of Allowance.
U.S. Appl. No. 10/787,073, Sep. 15, 2010, Issue Notification.
U.S. Appl. No. 11/152,562, Sep. 16, 2010, Notice of Allowance.
U.S. Appl. No. 11/427,297, Sep. 15, 2010, Office Action.
U.S. Appl. No. 11/767,818, Sep. 30, 2010, Office Action.
U.S. Appl. No. 12/365,397, Sep. 13, 2010, Office Action.
U.S. Appl. No. 10/356,214, Sep. 3, 2010, Notice of Allowance.
U.S. Appl. No. 10/435,104, Oct. 5, 2010, Notice of Allowance.
U.S. Appl. No. 10/682,459, Oct. 12, 2010, Office Action.
U.S. Appl. No. 11/406,203, Oct. 6, 2010, Issue Notification.
U.S. Appl. No. 11/532,576, Oct. 13, 2010, Notice of Allowance.
U.S. Appl. No. 11/958,281, Oct. 8, 2010, Office Action.
U.S. Appl. No. 12/114,031, Oct. 5, 2010, Office Action.
U.S. Appl. No. 12/403,277, Oct. 12, 2010, Office Action.
U.S. Appl. No. 11/508,715, Oct. 18, 2010, Office Action.
U.S. Appl. No. 10/667,144, Oct. 28, 2011, Notice of Allowance.
U.S. Appl. No. 12/945,646, Oct. 26, 2011, Office Action.
U.S. Appl. No. 10/264,306, Oct. 29, 2010, Notice of Allowance.
U.S. Appl. No. 12/106,928, Oct. 25, 2010, Office Action.
U.S. Appl. No. 11/198,811, Oct. 20, 2010, Issue Notification.
U.S. Appl. No. 11/508,662, Oct. 26, 2010, Office Action.
U.S. Appl. No. 11/852,190, Nov. 1, 2010, Office Action.
U.S. Appl. No. 12/114,091, Oct. 27, 2010, Office Action.
U.S. Appl. No. 11/427,297, Oct. 31, 2012, Issue Notification.
U.S. Appl. No. 12/114,091, Nov. 8, 2012, Office Action.
U.S. Appl. No. 12/403,277, Nov. 5, 2012, Office Action.
U.S. Appl. No. 12/481,377, Nov. 14, 2012, Issue Notification.
U.S. Appl. No. 12/608,769, Nov. 5, 2012, Notice of Allowance.
U.S. Appl. No. 12/684,400, Oct. 16, 2012, Office Action.
U.S. Appl. No. 12/848,642, Nov. 9, 2012, Office Action.
U.S. Appl. No. 12/850,242, Oct. 17, 2012, Office Action.
U.S. Appl. No. 13/039,087, Nov. 6, 2012, Notice of Allowance.
U.S. Appl. No. 11/427,309, Nov. 15, 2010, Office Action.
U.S. Appl. No. 10/517,004, Nov. 23, 2010, Issue Notification.
U.S. Appl. No. 12/114,031, Nov. 22, 2010, Office Action.
U.S. Appl. No. 12/403,256, Nov. 23, 2010, Issue Notification.
U.S. Appl. No. 12/338,977, Nov. 28, 2012, Office Action.
U.S. Appl. No. 12/961,331, Dec. 4, 2012, Office Action.
U.S. Appl. No. 13/030,922, Dec. 18, 2012, Office Action.
U.S. Appl. No. 12/897,358, filed Oct. 4, 2010, Carley.
U.S. Appl. No. 12/961,331, filed Dec. 6, 2010, Voss.
U.S. Appl. No. 12/966,923, Dec. 13, 2010, Cummins et al.
U.S. Appl. No. 10/147,774, Dec. 2, 2010, Notice of Allowance.
U.S. Appl. No. 10/541,083, Dec. 1, 2010, Issue Notification.
U.S. Appl. No. 11/048,503, Dec. 8, 2010, Issue Notification.
U.S. Appl. No. 11/959,334, Nov. 10, 2010, Issue Notification.
U.S. Appl. No. 12/393,877, Dec. 13, 2011, Office Action.
U.S. Appl. No. 12/941,809, Dec. 13, 2011, Restriction Requirement.
U.S. Appl. No. 12/955,859, Dec. 15, 2011, Office Action.
U.S. Appl. No. 12/113,851, Dec. 16, 2010, Office Action.
U.S. Appl. No. 12/114,091, Dec. 17, 2010, Office Action.
U.S. Appl. No. 12/684,470, Dec. 20, 2011, Restriction Requirement.
U.S. Appl. No. 12/684,569, Dec. 20, 2011, Restriction Requirement.
U.S. Appl. No. 11/675,462, Dec. 22, 2011, Notice of Allowance.
U.S. Appl. No. 14/017,039, filed Sep. 3, 2013, Ellingwood et al.
U.S. Appl. No. 14/023,428, filed Sep. 10, 2013, Ellingwood.
U.S. Appl. No. 10/786,444, Jul. 11, 2013, Notice of Allowance.
U.S. Appl. No. 10/908,721, Jul. 18, 2013, Notice of Allowance.
U.S. Appl. No. 11/396,141, Aug. 21, 2013, Office Action.
U.S. Appl. No. 11/411,925, Oct. 1, 2013, Office Action.
U.S. Appl. No. 11/427,309, Sep. 25, 2013, Issue Notification.
U.S. Appl. No. 11/532,325, Jul. 17, 2013, Office Action.
U.S. Appl. No. 11/744,089, Aug. 8, 2013, Notice of Allowance.
U.S. Appl. No. 12/106,928, Jun. 28, 2013, Office Action.
U.S. Appl. No. 12/850,242, Aug. 6, 2013, Notice of Allowance.
U.S. Appl. No. 12/941,809, Jul. 3, 2013, Office Action.
U.S. Appl. No. 12/955,859, Aug. 1, 2013, Notice of Allowance.
U.S. Appl. No. 12/961,331, Jul. 3, 2013, Office Action.
U.S. Appl. No. 12/961,331, Sep. 20, 2013, Advisory Action.
U.S. Appl. No. 13/026,989, Aug. 23, 2013, Office Action.
U.S. Appl. No. 13/028,041, Aug. 21, 2013, Notice of Allowance.
U.S. Appl. No. 13/030,922, Jul. 18, 2013, Office Action.
U.S. Appl. No. 13/308,227, Sep. 11, 2013, Office Action.
U.S. Appl. No. 13/525,839, Jul. 15, 2013, Notice of Allowance.
U.S. Appl. No. 13/791,829, Oct. 8, 2013, Notice of Allowance.
U.S. Appl. No. 13/898,202, filed May 20, 2013, Walberg et al.
U.S. Appl. No. 13/153,594, May 29, 2013, Office Action.
U.S. Appl. No. 13/791,829, May 29, 2013, Office Action.
U.S. Appl. No. 12/338,977, Jun. 19, 2013, Office Action.
U.S. Appl. No. 11/427,309, Jun. 7, 2013, Notice of Allowance.
U.S. Appl. No. 13/112,618, Jun. 7, 2013, Office Action.
U.S. Appl. No. 13/488,233, Jun. 5, 2013, Issue Notification.
U.S. Appl. No. 11/344,891, Jun. 26, 2013, Issue Notification.
U.S. Appl. No. 12/402,398, Jun. 26, 2013, Issue Notification.
U.S. Appl. No. 13/112,631, Jun. 26, 2013, Office Action.
U.S. Appl. No. 12/402,398, Jan. 24, 2011, Office Action.
U.S. Appl. No. 12/945,646, Jan. 20, 2011, Office Action.
U.S. Appl. No. 13/030,922, filed Feb. 18, 2011, Cummins.
U.S. Appl. No. 13/039,087, Mar. 2, 2011, Palermo et al.
U.S. Appl. No. 10/356,214, Feb. 23, 2011, Issue Notification.
U.S. Appl. No. 10/435,104, Jul. 23, 2009, Notice of Allowance.
U.S. Appl. No. 10/669,313, Oct. 31, 2005, Office Action.
U.S. Appl. No. 11/113,549, Jul. 6, 2010, Office Action.
U.S. Appl. No. 11/959,334, Jul. 23, 2010 Notice of Allowance.
U.S. Appl. No. 12/403,277, Jul. 8, 2010, Office Action.
U.S. Appl. No. 12/122,603, Sep. 23, 2011, Office Action.
U.S. Appl. No. 12/113,092, filed Apr. 30, 2008, Ginn et al.
U.S. Appl. No. 12/143,020, Jun. 20, 2008, Ellingwood et al.
U.S. Appl. No. 60/843,325, Sep. 8, 2006, Carly.
U.S. Appl. No. 60/946,030, Jun. 25, 2007, Voss et al.
U.S. Appl. No. 60/946042, Jun. 25, 2007, Ellingwood et al.
Database WPI; Section PQ, Week 200120; Derwent Publications Ltd., London GB; Class P31, AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
"Hand tool for forming telephone connections—comprises pliers with reciprocably driven ram crimping clip around conductors against anvil", Derwent-ACC-No: 1978-B8090A.

(56) References Cited

OTHER PUBLICATIONS

DL Wessel et al, Outpatient closure of the patent ductus arteriosus, Circulation, May 1988, pp. 1068-1071, vol. 77—No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, the Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
McCarthy, et al., "Tension (Stay) Suture Bridge", J. of International College of Surgeons, 34(5), pp. 613-614 (Nov. 1960). cited by other.
MD Gonze et al, Complications associated with percutaneous closure devices, Conference: Annual Meeting of the Society for Clinical Vascular Surgery, the American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Stretch Comb by Scunci, retrieved via internet at www.scunci.com/productdetail by examiner on Oct. 9, 2007, publication date unavailable.
Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5—No. 3-4.
UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.
U.S. Appl. No. 09/478,179, Nov. 6, 2000, Notice of Allowance.
U.S. Appl. No. 09/478,179, Feb. 15, 2001, Issue Notification.
U.S. Appl. No. 09/546,998, May 6, 2002, Notice of Allowance.
U.S. Appl. No. 09/546,998, Sep. 19, 2002, Issue Notification.
U.S. Appl. No. 09/610,238, Mar. 26, 2001, Notice of Allowance.
U.S. Appl. No. 09/610,238, Sep. 5, 2001, Office Action.
U.S. Appl. No. 09/610,238, Feb. 11, 2002, Notice of Allowance.
U.S. Appl. No. 09/732,178, Aug. 1, 2002, Office Action.
U.S. Appl. No. 09/732,178, Dec. 24, 2002, Office Action.
U.S. Appl. No. 09/732,178, Jun. 10, 2003, Office Action.
U.S. Appl. No. 09/732,178, Jul. 3, 2003, Office Action.
U.S. Appl. No. 09/732,178, Nov. 17, 2003, Notice of Allowance.
U.S. Appl. No. 09/732,178, Mar. 25, 2004, Issue Notification.
U.S. Appl. No. 09/732,835, Sep. 11, 2003, Office Action.
U.S. Appl. No. 09/732,835, Feb. 9, 2004, Office Action.
U.S. Appl. No. 09/732,835, Mar. 17, 2004, Notice of Allowance.
U.S. Appl. No. 09/764,813, Mar. 26, 2001, Office Action.
U.S. Appl. No. 09/764,813, Jun. 4, 2001, Notice of Allowance.
U.S. Appl. No. 09/764,813, Aug. 6, 2001, Issue Notification.
U.S. Appl. No. 09/933,299, Feb. 26, 2003, Office Action.
U.S. Appl. No. 09/933,299, Jun. 16, 2003, Notice of Allowance.
U.S. Appl. No. 09/933,299, Sep. 25, 2003, Issue Notification.
U.S. Appl. No. 09/948,813, Jan. 31, 2003, Notice of Allowance.

(56) References Cited

OTHER PUBLICATIONS

U.S. Appl. No. 09/948,813, Jun. 5, 2003, Issue Notification.
U.S. Appl. No. 09/949,398, Mar. 4, 2003, Office Action.
U.S. Appl. No. 09/949,398, Jul. 28, 2003, Notice of Allowance.
U.S. Appl. No. 09/949,398, Dec. 11, 2003, Issue Notification.
U.S. Appl. No. 09/949,438, Dec. 17, 2002, Office Action.
U.S. Appl. No. 09/949,438, Apr. 21, 2003, Notice of Allowance.
U.S. Appl. No. 09/949,438, Aug. 21, 2003, Issue Notification.
U.S. Appl. No. 10/006,400, Aug. 27, 2004, Office Action.
U.S. Appl. No. 10/006,400, Feb. 23, 2005, Office Action.
U.S. Appl. No. 10/006,400, Apr. 11, 2005, Office Action.
U.S. Appl. No. 10/006,400, Jul. 27, 2005, Office Action.
U.S. Appl. No. 10/006,400, Mar. 6, 2006, Office Action.
U.S. Appl. No. 10/006,400, May 24, 2006, Office Action.
U.S. Appl. No. 10/006,400, Oct. 26, 2006, Office Action.
U.S. Appl. No. 10/006,400, Apr. 19, 2007, Office Action.
U.S. Appl. No. 10/006,400, Apr. 2, 2008, Office Action.
U.S. Appl. No. 10/081,717, Sep. 29, 2003, Notice of Allowance.
U.S. Appl. No. 10/081,717, Feb. 5, 2004, Issue Notification.
U.S. Appl. No. 10/081,723, Sep. 29, 2004, Office Action.
U.S. Appl. No. 10/081,723, May 13, 2005, Notice of Allowance.
U.S. Appl. No. 10/081,725, Feb. 9, 2004, Notice of Allowance.
U.S. Appl. No. 10/081,725, Apr. 13, 2004, Office Action.
U.S. Appl. No. 10/081,725, May 27, 2004, Issue Notification.
U.S. Appl. No. 10/081,726, Apr. 11, 2003, Notice of Allowance.
U.S. Appl. No. 10/081,726, Jun. 9, 2003, Examiner's Amendment.
U.S. Appl. No. 10/147,774, Nov. 4, 2004, Office Action.
U.S. Appl. No. 10/147,774, May 4, 2005, Office Action.
U.S. Appl. No. 10/147,774, Oct. 18, 2005, Office Action.
U.S. Appl. No. 10/147,774, Apr. 18, 2007, Notice of Allowance.
U.S. Appl. No. 10/147,774, Sep. 27, 2007, Notice of Allowance.
U.S. Appl. No. 10/147,774, Feb. 4, 2008, Notice of Allowance.
U.S. Appl. No. 10/147,774, Jun. 30, 2008, Office Action.
U.S. Appl. No. 10/240,183, Jul. 27, 2004, Office Action.
U.S. Appl. No. 10/240,183, Dec. 17, 2004, Office Action.
U.S. Appl. No. 10/240,183, Mar. 9, 2005, Notice of Allowance.
U.S. Appl. No. 10/240,183, Aug. 11, 2006, Response to § 312 Amendment.
U.S. Appl. No. 10/264,306, Feb. 9, 2005, Office Action.
U.S. Appl. No. 14/246,926, filed Apr. 7, 2014, Carley et al.
U.S. Appl. No. 14/246,973, filed Apr. 1, 2014, Carley et al.
Turn—macmillandictionary.com/dictionary.american/turn 2013.
Turn—Merriam-webster.com/dictionary/turn 2013.
U.S. Appl. No. 11/113,549, Mar. 14, 2014, Notice of Allowance.
U.S. Appl. No. 11/396,141, Nov. 4, 2013, Notice of Allowance.
U.S. Appl. No. 11/411,925, Feb. 5, 2014, Notice of Allowance.
U.S. Appl. No. 11/455,993, Jan. 29, 2014, Office Action.
U.S. Appl. No. 11/532,325, Dec. 2, 2013, Office Action.
U.S. Appl. No. 11/674,930, Apr. 3, 2014, Notice of Allowance.
U.S. Appl. No. 11/852,190, Nov. 26, 2013, Office Action.
U.S. Appl. No. 11/852,190, Feb. 12, 2014, Notice of Allowance.
U.S. Appl. No. 12/106,928, Dec. 2, 2013, Office Action.
U.S. Appl. No. 12/106,928, Mar. 25, 2014, Advisory Action.
U.S. Appl. No. 12/113,851, Mar. 17, 2014, Office Action.
U.S. Appl. No. 12/114,031, Mar. 10, 2014, Office Action.
U.S. Appl. No. 12/122,603, Nov. 20, 2013, Office Action.
U.S. Appl. No. 12/403,277, Jan. 27, 2014, Office Action.
U.S. Appl. No. 12/642,319, Dec. 16, 2013, Office Action.
U.S. Appl. No. 12/688,065, Oct. 18, 2013, Office Action.
U.S. Appl. No. 12/688,065, Apr. 8, 2014, Office Action.
U.S. Appl. No. 12/848,642, Feb. 3, 2014, Notice of Allowance.
U.S. Appl. No. 12/941,809, Nov. 8, 2013, Office Action.
U.S. Appl. No. 12/941,809, Feb. 3, 2014, Notice of Allowance.
U.S. Appl. No. 12/987,792, Jan. 21, 2014, Office Action.
U.S. Appl. No. 13/030,922, Jan. 8, 2014, Notice of Allowance.
U.S. Appl. No. 13/112,618, Nov. 20, 2013, Office Action.
U.S. Appl. No. 13/112,631, Dec. 2, 2013, Office Action.
U.S. Appl. No. 13/153,594, Oct. 16, 2013, Notice of Allowance.
U.S. Appl. No. 13/222,899, Jan. 10, 2014, Office Action.
U.S. Appl. No. 13/898,202, Jan. 3, 2014, Office Action.
U.S. Appl. No. 12/402,398, Mar. 13, 2013, Notice of Allowance.
U.S. Appl. No. 13/028,041, Jan. 4, 2013, Office Action.
U.S. Appl. No. 13/028,041, Feb. 26, 2013, Office Action.
U.S. Appl. No. 10/638,115, Feb. 22, 2010, Issue Notification.
U.S. Appl. No. 14/539,830, Nov. 12, 2014, Clark.
U.S. Appl. No. 14/562,467, Dec. 5, 2014, Ellingwood et al.
U.S. Appl. No. 11/396,731, Feb. 12, 2015, Office Action.
U.S. Appl. No. 11/455,993, Aug. 11, 2014, Notice of Allowance.
U.S. Appl. No. 11/532325, Jan. 16, 2015, Notice of Allowance.
U.S. Appl. No. 11/958,295, Jun. 13, 2014, Notice of Allowance.
U.S. Appl. No. 12/106,928, Oct. 3, 2014, Notice of Allowance.
U.S. Appl. No. 12/113,851, Aug. 21, 2014, Office Action.
U.S. Appl. No. 12/113,851, Feb. 20, 2015, Notice of Allowance.
U.S. Appl. No. 12/114,091, Feb. 12, 2015, Office Action.
U.S. Appl. No. 12/122,603, Apr. 30, 2014, Office Action.
U.S. Appl. No. 12/393,877, Aug. 4, 2014, Notice of Allowance.
U.S. Appl. No. 12/403,277, Aug. 15, 2014, Office Action.
U.S. Appl. No. 12/548,274, Aug. 14, 2014, Office Action.
U.S. Appl. No. 12/608,773, Jul. 17, 2014, Office Action.
U.S. Appl. No. 12/642,319, May 27, 2014, Notice of Allowance.
U.S. Appl. No. 12/684,400, Feb. 23, 2015, Office Action.
U.S. Appl. No. 12/684,470, Jun. 4, 2014, Office Action.
U.S. Appl. No. 12/684,470, Nov. 14, 2014, Office Action.
U.S. Appl. No. 12/684,542, Jun. 18, 2014, Office Action.
U.S. Appl. No. 12/684,542, Dec. 1, 2014, Office Action.
U.S. Appl. No. 12/684,562, Sep. 10, 2014, Office Action.
U.S. Appl. No. 12/684,562, Feb. 17, 2015, Notice of Allowance.
U.S. Appl. No. 12/684,569, Apr. 23, 2014, Office Action.
U.S. Appl. No. 12/950,628, Apr. 25, 2014, Notice of Allowance.
U.S. Appl. No. 12/961,331, Apr. 25, 2014, Notice of Allowance.
U.S. Appl. No. 12/987,792, Jun. 11, 2014, Office Action.
U.S. Appl. No. 12/987,792, Aug. 25, 2014, Notice of Allowance.
U.S. Appl. No. 13/112,618, Dec. 15, 2014, Office Action.
U.S. Appl. No. 13/112,631, Nov. 20, 2014, Office Action.
U.S. Appl. No. 13/222,899, Jul. 31, 2014, Office Action.
U.S. Appl. No. 13/898,202, Aug. 21, 2014, Office Action.
U.S. Appl. No. 13/898,202, Feb. 10, 2015, Notice of Allowance.
U.S. Appl. No. 14/017,039, Jan. 23, 2015, Office Action.
U.S. Appl. No. 12/393,877, Sep. 29, 2011, Office Action.
U.S. Appl. No. 12/608,773, Mar. 12, 2015, Office Action.
U.S. Appl. No. 13/222,899, Apr. 1, 2015, Office Action.

* cited by examiner

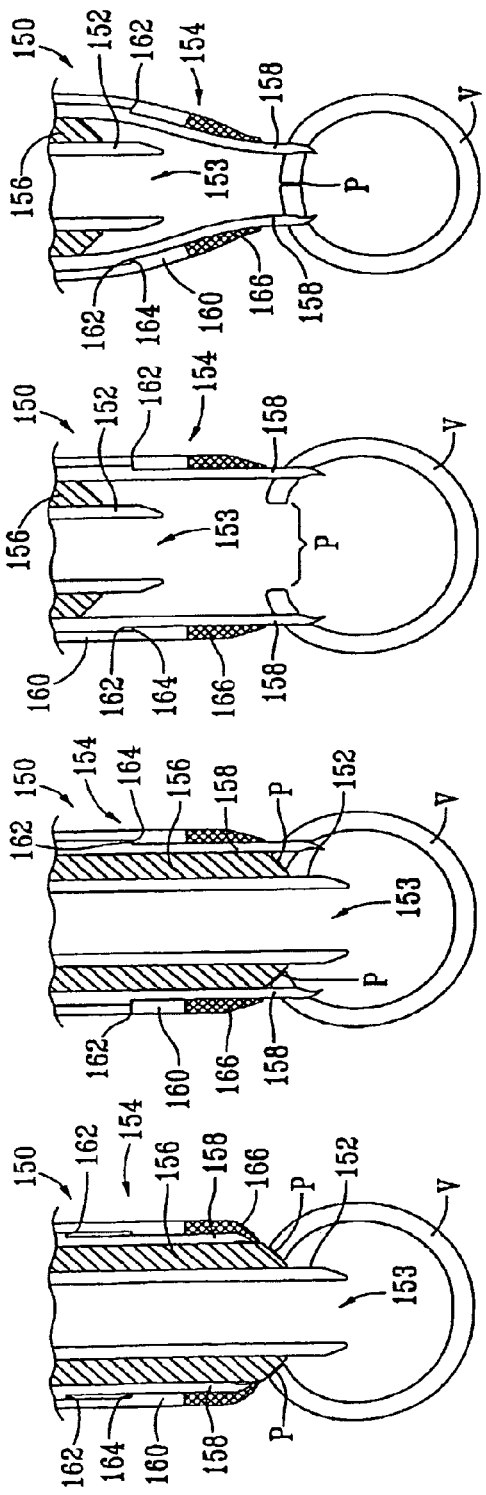
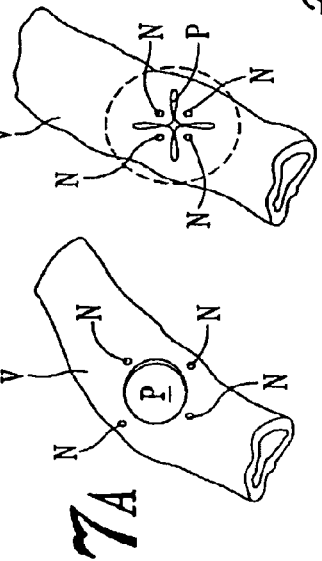
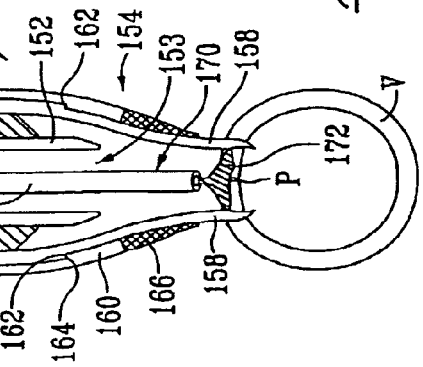
Fig. 6A, Fig. 6B, Fig. 6C, Fig. 6D, Fig. 6E, Fig. 7A, Fig. 7B

INTEGRATED VASCULAR DEVICE WITH PUNCTURE SITE CLOSURE COMPONENT AND SEALANT AND METHODS OF USE

CROSS-REFERENCE TO RELATED APPLICATIONS

This application is a divisional of U.S. patent application Ser. No. 10/147,774, filed May 17, 2002, which is a continuation of U.S. patent application Ser. No. 09/610,238, filed Jul. 5, 2000, now U.S. Pat. No. 6,391,048, which is a continuation-in-part of U.S. patent application Ser. No. 09/478,179 filed Jan. 5, 2000, now U.S. Pat. No. 6,197,042, the disclosures of which are each incorporated by reference herein.

BACKGROUND OF THE INVENTION

1. The Field of the Invention

The present invention relates to apparatus and methods for sealing an iatrogenic puncture in a vessel formed in conjunction with a diagnostic or therapeutic treatment. More particularly, the present invention provides an integrated vascular device comprising a sheath having a puncture closure components and puncture sealant.

2. The Relevant Technology

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al. describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art. Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, such devices employing resilient or deformable clips have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft having a distal end formed with one or more opposed pairs of resilient grasping prongs and that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site.

The use of backbleed indication as a positioning technique within a vascular puncture is known. For example, U.S. Pat. No. 4,317,445 to Robinson describes a flashback chamber for providing visual indication of venous entry of a cannula. However, that device does not discuss vascular wound closure. U.S. Pat. No. 5,676,689 to Kensey et al., which claims priority from the U.S. Pat. No. 5,222,974 patent discussed above, uses a vessel location device to simplify positioning of the biodegradable plug. The vessel locator enables blood from the vessel to flow there through so that the position of the vessel may be determined. However, the Kensey system only proffers one closure device, and that device is complex and raises concerns about biocompatibility. It also requires the closure component to be positioned within the puncture, thereby increasing the likelihood of dangerous over-advancement of the plug into the vessel.

The percutaneous puncture closure devices described in the foregoing patents generally have the drawback that they require relatively complex mechanisms and require time consuming manipulation to achieve hemostasis. It therefore would be desirable to provide apparatus and methods suitable for vascular puncture closure that overcome these disadvantages of previously known devices.

It also would be desirable to provide apparatus and methods that quickly and effectively achieve hemostasis.

It further would be desirable to provide apparatus and methods wherein all foreign materials left in a patient's body are bioabsorbable.

It still further would be desirable to provide vascular puncture closure apparatus and methods that are safe, low cost, and easy to use.

BRIEF SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostasis.

It further is an object of the present invention to provide apparatus and methods wherein all foreign materials left in a patient's body are bioabsorbable.

It still further is an object of the present invention to provide vascular puncture closure apparatus and methods that are safe, low cost, and easy to use.

These and other objects of the present invention are accomplished by providing an integrated vascular device comprising a sheath having a puncture closure component and puncture sealant. The closure component is disposed on and advanceable over the exterior of the sheath, which may, for example, comprise an introducer sheath, a trocar, or a catheter. The closure component may comprise any of a variety of apparatus suited to close a vascular puncture. Once the closure component has been actuated to close the puncture, sealant is introduced to the exterior surface of closed puncture, preferably through the sheath's interior lumen, where the sealant seals the puncture closed. The sheath with closure component is then removed from the patient.

In a preferred embodiment constructed in accordance with the present invention, the closure component comprises a twist closure device. The device pierces tissue surrounding the vascular puncture and then is rotated to close the wound. In an alternative embodiment, the closure component comprises needles and an elastic segment surrounding the needles. The needles pierce the puncture with the elastic segment expanded. The segment is then allowed to resiliently contract to an unstressed configuration of smaller diameter, thereby drawing the needles together and closing the wound.

In a still further alternative embodiment, the needles, or prongs, are elastically deformed to an expanded diameter, in which they pierce the tissue adjacent to puncture. The needles then are allowed to resiliently contract to an unstressed configuration of smaller diameter, thereby closing the wound.

Sealant then may be introduced, preferably through the interior lumen of the sheath, to seal the puncture closed. The sealant may comprise any of a variety of sealants, per se known, including adhesives, sutures, and clips, all of which are preferably bioabsorbable. Alternatively, the closure component may further comprise the sealant, wherein the closure component is left in place within the vessel until hemostasis naturally occurs, or wherein the closure component comprises a monopolar electrode or opposed bipolar electrodes that cauterize the wound with RF current. In addition to cauterization, RF energy generates heat that beneficially causes shrinkage of the vascular tissue, thereby assisting closure of the wound. Thermal energy from electrical induction, infrared light, ultrasonic vibration, microwave or laser irradiation, and other means may also be used to seal the puncture.

Advantageously, the puncture closure component of the present invention is inexpensively integrated into a sheath, thereby minimizing mechanical complexity while providing quick, safe, effective, and easy-to-use apparatus for achieving vascular closure that overcomes drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 6A-6E are side-sectional views of a further alternative embodiment in use at a vascular puncture site, illustrating a method of sealing the puncture site; and FIGS. 7A and 7B are isometric views of a section of vessel including and corresponding to the vascular puncture site of FIG. 6, further illustrating the method of FIG. 6.

DETAILED DESCRIPTION OF THE PREFERRED EMBODIMENTS

The integrated vascular sheath with closure component of the present invention overcomes disadvantages associated with previously known methods and apparatus for sealing a vascular puncture by providing a quick, simple, safe, low cost, effective, and easy-to-use solution to wound closure. Apparatus constructed in accordance with the present invention provide vascular access and wound closure in a single device, eliminating the time and manipulation required to insert a separate closure device at the completion of a procedure.

Figure 1:
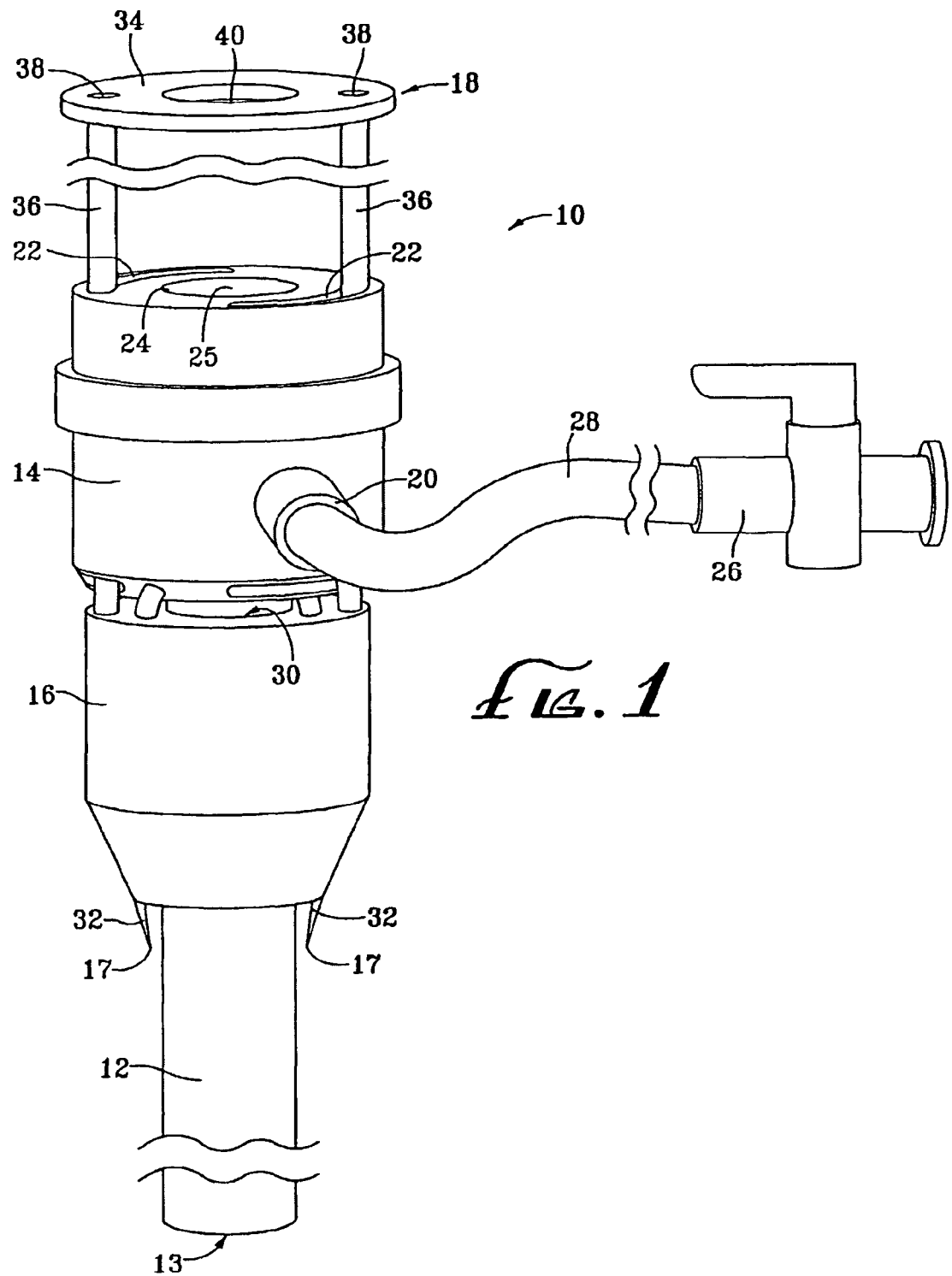
FIG. 1 is a side view of a preferred embodiment of an integrated vascular device constructed in accordance with the present invention.

Referring to FIG. 1, a first embodiment of apparatus of the present invention is described. Vascular device 10 comprises sheath 12 coupled to hub 14, closure component 16, and closure actuator 18.

Sheath 12, which may, for example, comprise an introducer sheath, a trocar, or a catheter, includes central lumen 13 through which other devices may be introduced into the vasculature, for example, to perform a diagnostic or interventional procedure such as angiography, angioplasty, or stenting, or to seal a puncture site.

Hub 14 is mounted on the proximal end of sheath 12 and includes side port 20, arc lumens 22, and device port 24. Device port 24 communicates with central lumen 13 of sheath 12, and has self-sealing elastomeric membrane 25 disposed across it. Self-sealing membrane 25, which may comprise, for example, latex or a biocompatible synthetic rubber, permits interventional devices to be introduced through device port 24, while preventing blood loss through central lumen 13. Side port 20 of hub 14 is also in communication with central lumen 13, and is connected to hemostatic port 26 via biocompatible tubing 28.

In accordance with the principles of the present invention, closure component 16 comprises lumen 30 that receives sheath 12. Component 16 is slidably disposed on the exterior of sheath 12 and is movable from a stowed position, adjacent hub 14, to a distal deployment position, where tines 17 of component 16 are urged into engagement with tissue surrounding a vascular puncture. Closure component 16 comprises at least two sharpened tips, or tines 17. Tines 17 preferably comprise backbleed ports 32. Closure component 16 is rotatable within arc-lumens 22 about the longitudinal axis of sheath 12, so that, with tines 17 engaging tissue surrounding the vascular puncture, component 16 closes the puncture.

Closure actuator 18 comprises plunger 34 and tubes 36, which are configured to slidably pass through arc lumens 22 of hub 14. The proximal ends of tubes 36 are coupled to backbleed bores 38 of plunger 34. The distal ends of tubes 36 are mounted, either permanently or detachably, in closure component 16, so that movement of plunger 34 causes corresponding proximal or distal movement of closure component 16. Likewise, rotation of plunger 34 causes corresponding rotation of tubes 36 within arc lumens 22, which, in turn, rotates closure component 16 about the longitudinal axis of sheath 12.

Plunger 34 further comprises device bore 40, coaxially aligned with device port 24, and through which interventional devices or puncture sealants may be passed. As described in detail hereinafter, when plunger 34 is moved to its proximal-most position, closure component 16 is disposed adjacent to hub 14 and preferably provides adequate clearance for interventional devices to be inserted through device port 24 and central lumen 13 into the patient's vasculature. When moved to its distal-most position, plunger 34 causes tubes 36 to urge closure component 16 distally. Interventional devices or sealants then may be introduced through device bore 40, device port 24, and central lumen 13 into the vasculature.

Backbleed bores 38 of plunger 32 are in communication with backbleed lumens (not shown) within tubes 36. The backbleed lumens of tubes 36 are in communication with backbleed ports 32 of tines 17, thereby establishing a complete backbleed path through ports 32, the lumens (not shown) of tubes 36, and bores 38. When tines 17 of closure component 16 pierce a vessel wall surrounding a vascular puncture, blood enters backbleed ports 32 and exits through backbleed bores 38, providing visual confirmation to a surgeon that tines 17 are positioned within the vessel wall. The backbleed path thus enables the surgeon to determine when closure component 16 has been sufficiently advanced to permit rotation of component 16 to close the puncture, while reducing the risk that component 16 is either short of the puncture site or is extended into the vessel.

In conjunction with closure of the puncture site caused by rotation of component 16, a puncture sealant may be introduced to the puncture site to seal the site closed. The sealant may, for example, comprise an adhesive, such as a bioglue, tissue sealant, or clotting agent, delivered through hemostatic port 26, biocompatible tubing 28, side port 20 and central lumen 13 of introducer sheath 12 to the vascular puncture to further help seal the vessel after puncture closure with closure component 16. Alternatively, the adhesive may be delivered through device port 24 or through the backbleed path described above. Instead of adhesives, the closure component may further comprise the sealant, wherein the closure component is left in place within the vessel until hemostasis naturally occurs. The sealant may also comprise sutures delivered through central lumen 13. Additionally, the sealant may comprise thermal energy application from, for example, electrical induction, infrared light, ultrasonic vibration, microwave or laser irradiation, and other means.

Figure 2:
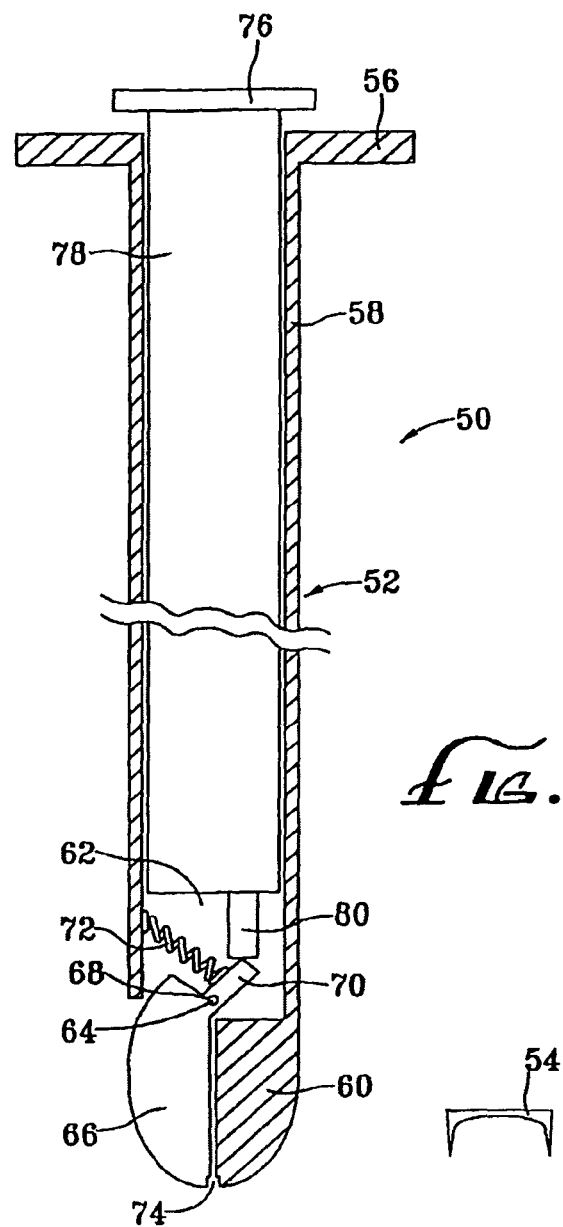
FIG. 2 is a side-sectional view of a sealing device for use with the vascular device of FIG. 1.

With reference to FIG. 2, an alternative puncture sealing device in accordance with the present invention is described. Sealing device 50 comprises delivery device 52 and clip 54. Delivery device 52 comprises proximal end 56 attached to tube 58. Tube 58 terminates at first jaw 60 at its distal end and further comprises lumen 62 and pin 64. Pin 64 extends into lumen 62 from an interior surface of tube 58 and is disposed perpendicular to the longitudinal axis of tube 58.

Delivery device 52 further comprises second jaw 66 having female connector 68 coupled to pin 64, so that second jaw 66 pivots about pin 64. Second jaw 66 further comprises moment arm 70. Tension spring 72 is coupled to moment arm 70 and to the interior surface of tube 58 in a manner that biases second jaw 66 against first jaw 60.

First jaw 60 and second jaw 66 preferably form channel 74 when biased against one another. Channel 74 is configured to receive clip 54. The biasing force applied by tension spring 72 holds clip 54 within channel 74, so that the clip may be advanced into tissue surrounding a vascular puncture that has had its edges approximated by closure component 16 (FIG. 1).

Delivery device 52 still further comprises plunger 76 coupled to pushrod 78 having release arm 80. Pushrod 78 is received within lumen 62 of tube 58, so that release arm 80 engages moment arm 70.

Distal advancement of pushrod 78, via application of force to plunger 76, causes release arm 80 to urge moment arm 70 distally. This motion overcomes the biasing force applied by tension spring 72 and causes second jaw 66 to pivot about pin 64. Second jaw 66 thus no longer contacts first jaw 60, and clip 54 is released from channel 74. Tube 58, first jaw 60, second jaw 66, and clip 54 of sealing device 50 preferably are sized for introduction into a patient's vasculature through device bore 40, device port 24, and lumen 13 of vascular device 10.

Referring to FIGS. 3A-3D through 4A-4D, in conjunction with FIGS. 1 and 2, a method of using vascular device 10 with sealing device 50 is described. Sheath 12 is advanced through skin, fat, and muscle tissue into vessel V, through the vessel wall tissue surrounding vascular puncture P. With plunger 34 and tubes 36 of actuator 18 in the proximal-most, fully retracted position, an interventional procedure is performed by introducing one or more interventional devices, e.g. angioplasty balloons, stent delivery systems, atherectomy devices, etc., through device port 24 and lumen 13 of sheath 12, in accordance with well-known techniques. Side port 20 may be used to infuse fluids, e.g., contrast agents or medications, into the vessel through sheath 12 during the interventional procedure.

Upon completion of the procedure, vascular device 10 may be advantageously used to close vascular puncture P. At this point, closure actuator 18 and closure component 16 are disposed in the proximal-most position, with component 16 adjacent to hub 14. Closure actuator 18 is advanced by urging plunger 34 in the distal direction, thus causing tubes 36 to slide through arc lumens 22 of hub 14 and advance closure component 16.

Figure 3A:
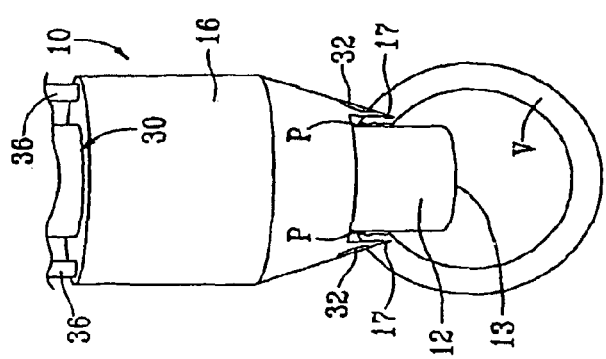
FIGS. 3A-3D are side views of the closure component of FIG. 1 in use at a vascular puncture site, shown in section, with the sealing device of FIG. 2, illustrating a method of sealing the puncture site.
Figure 4A:
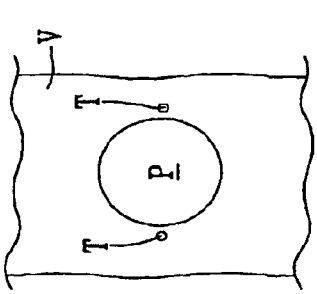
FIGS. 4A-4D are top views of the vascular puncture site of FIG. 3, corresponding to the side-sectional views of FIG. 3, further illustrating the method of FIG. 3.

As seen in FIG. 3A, continued distal advancement of plunger 34 causes tines 17 at the distal end of closure component 16 to pierce tissue surrounding puncture P, so that the backbleed ports 32 of tines 17 directly communicate with the puncture wound. Tine punctures T in FIG. 4A represent the points at which tines 17 enter vessel V. The presence of pressure in the vessel higher than atmospheric pressure causes blood to pass through backbleed ports 32, through the backbleed lumens (not shown) of tubes 36, and exit through the proximal ends of backbleed bores 38, thus confirming that tines 17 have engaged tissue around the puncture site and should not be advanced further.

Figure 3B:
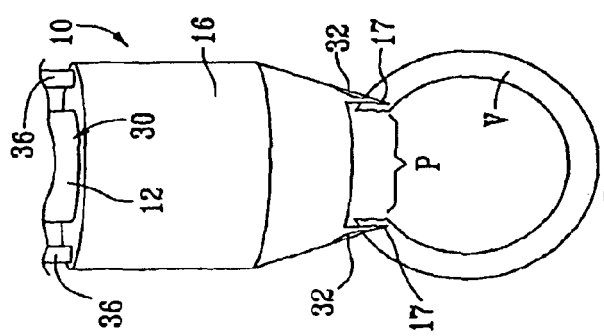
Figure 4B:
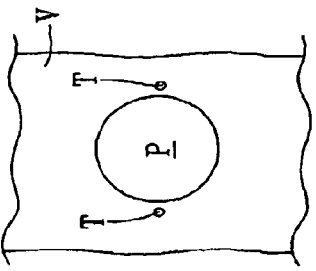
Figure 3C:
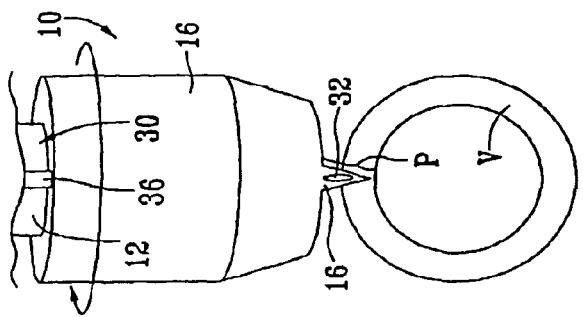
Figure 4C:
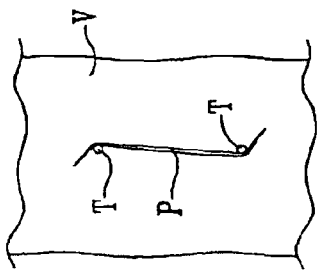

In FIG. 3B, sheath 12 is removed from puncture P to facilitate closure of the puncture. Closure actuator 18 is held stationary while hub 14 is withdrawn proximally, thereby withdrawing sheath 12 proximally from puncture P. The puncture remains open, as seen in FIG. 4B. With sheath 12 no longer within puncture P, closure actuator 18 is rotated within arc lumens 22 to rotate closure component 16. Rotation of closure component 16 causes tines 17 to rotate and urge the puncture closed, as seen in FIGS. 3C and 4C.

Upon closure of puncture P, a sealant is introduced to seal the wound closed. The sealant may, for example, comprise an adhesive, such as a bioglue, tissue sealant, or clotting agent, it may comprise a suture, it may comprise thermal energy application, or it may comprise leaving the closure component in place within vessel V until hemostasis naturally occurs. Alternatively, the sealing device may comprise a clip, as described hereinafter.

Figure 3D:
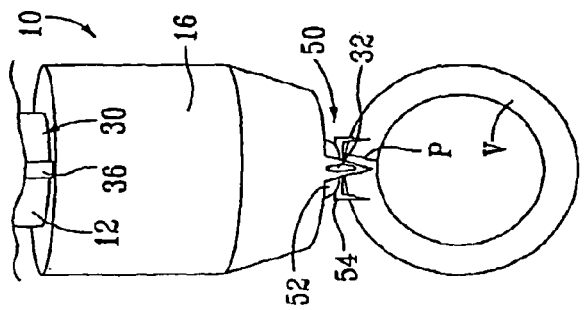
Figure 4D:
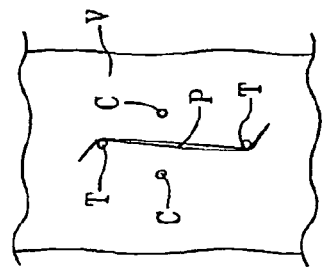

FIGS. 3D and 4D show apparatus 10 used in conjunction with sealing device 50 of FIG. 2. With clip 54 disposed in channel 74 of delivery device 52, the delivery device is delivered to vessel V through device bore 40 of closure actuator 18, device port 24 of hub 14, and central lumen 13 of sheath 12. Clip 54 punctures the vessel at tissue surrounding closed puncture P, creating clip punctures C and sealing the puncture. Pushrod 78 of delivery device 52 is then actuated to separate second jaw 66 from first jaw 60 to release clip 54 from delivery device 52. Apparatus 10 and delivery device 52 are removed from the patient to complete the procedure. Clip 54 maintains closure until hemostasis occurs and is preferably bioabsorbable so that no foreign materials are permanently implanted in the patient's body. Additional clips may also be implanted, as required.

Figures 5A, 5B, 5C:
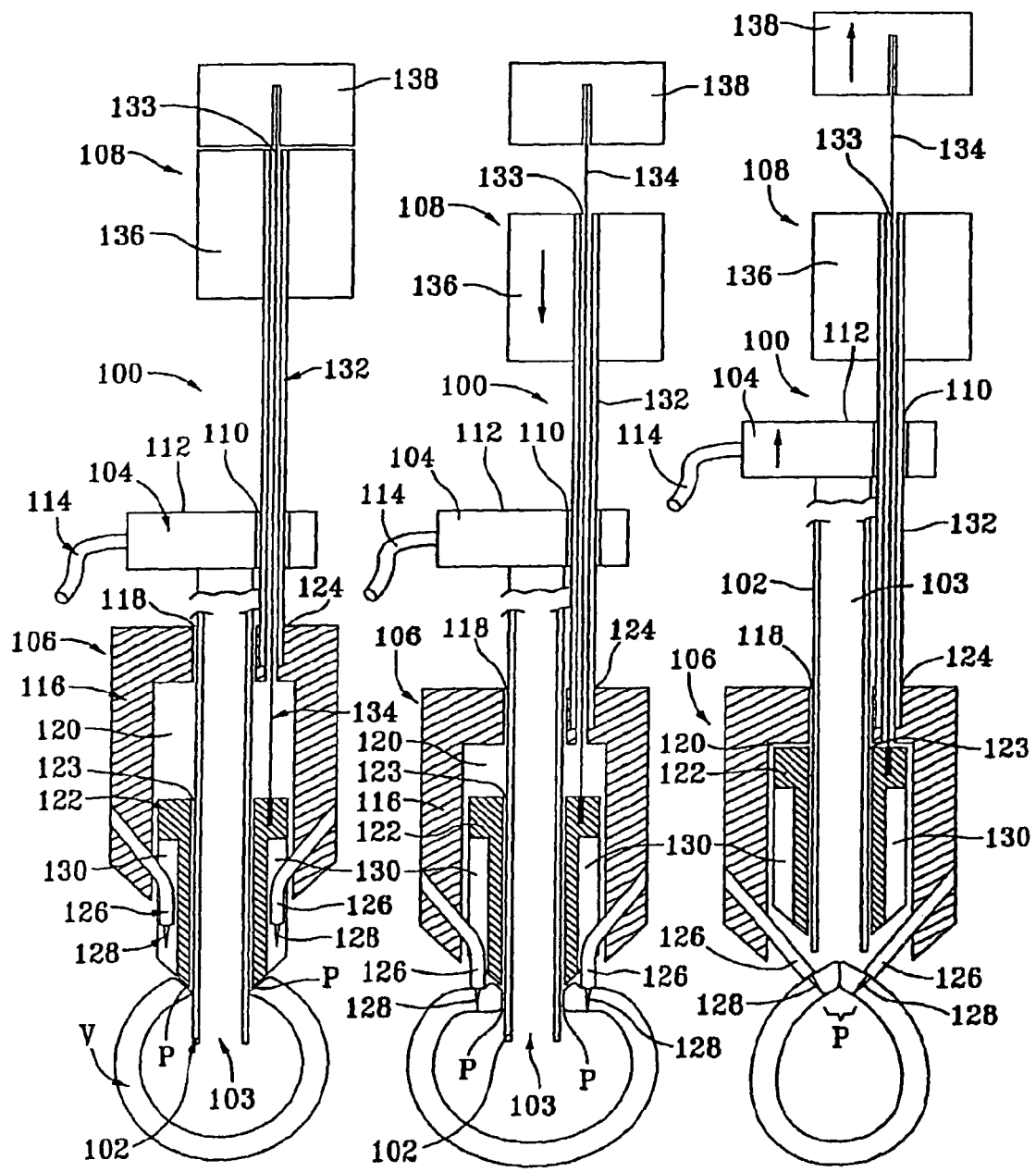
FIGS. 5A-5C are side-sectional views of an alternative embodiment of an integrated vascular device of the present invention in use at a vascular puncture site, illustrating a method of sealing the puncture site.

With reference now to FIGS. 5A-5C, an alternative integrated vascular device in accordance with the present invention is described. Apparatus 100 comprises sheath 102 coupled to hub 104, closure component 106, and closure actuator 108.

Like sheath 12, sheath 102 may, for example, comprise an introducer sheath, a trocar, or a catheter, and includes central lumen 103 through which other devices may be introduced into the vasculature, for example, to perform a diagnostic or interventional procedure such as angiography, angioplasty, or stenting, or to seal a puncture site. Hub 104 comprises bore 110, which slidably receives actuator 108, and device port 112, which is in communication with central lumen 103 of sheath 102 and permits introduction of interventional devices while preventing blood loss through central lumen 103. Hub 104 further comprises side port 114.

Closure component 106 comprises outer housing 116 having lumen 118 configured to slidably receive sheath 102, bore 120 for slidably receiving inner housing 122, lumen 124 adapted to receive closure actuator 108, and needles or prongs 126 with sharpened tips 128. Inner housing 122 has lumen 123 adapted to receive sheath 102 and channels 130 adapted to receive prongs 126. Component 106 comprises at least two prongs 126, and preferably comprises four.

Closure actuator 108 comprises actuation tube 132 having lumen 133, actuation rod 134 disposed within actuation tube 132, first plunger 136 coupled to the proximal end of tube 132, and second plunger 138 coupled to the proximal end of rod 134. The distal end of tube 132 is affixed, either permanently or detachably, in lumen 124 to outer housing 116 of closure component 106, while the distal end of rod 134 is coupled to inner housing 122.

To perform an interventional procedure through central lumen 103 of sheath 102, the sheath is advanced through skin, fat, and muscle tissue into vessel V, through vascular puncture P, in accordance with well-known techniques. With closure component 106 in the proximal-most, fully retracted position adjacent hub 104, the interventional procedure then is performed by introducing one or more interventional devices, e.g. angioplasty balloons, stent delivery systems, atherectomy devices, etc., through device port 112 and lumen 103 of sheath 102, again in accordance with well-known techniques. Side port 114 may be used to infuse fluids, e.g., contrast agents or medications, into the vessel through sheath 102 during the interventional procedure.

Upon completion of the procedure, apparatus 100 advantageously may be used to close the vessel. Closure component 106 is advanced distally by urging plungers 136 and 138 distally. Inner housing 122 is only partially received within bore 120 of outer housing 116 so that prongs 126 are elastically deformed and received within channels 130. As shown in FIG. 5A, closure component 106 is advanced until inner housing 122 abuts against the vessel V, as may be determined, for example, with a backbleed indicator (not shown).

In FIG. 5B, first plunger 136 is urged distally to distally advance actuation tube 132 and outer housing 116, while second plunger 138 and sheath 102 are held stationary. Advancement of outer housing 116 advances sharpened tips 128 of prongs 126 into tissue surrounding puncture P.

In FIG. 5C, sheath 102 and second plunger 138 are retracted proximally to draw sheath 102 out of vessel V and to draw inner housing 122 completely within bore 120 of outer housing 116. Proximally retracting inner housing 122 via actuation rod 134 and second plunger 138 removes prongs 126 of outer housing 116 from channels 130 of the inner housing. The prongs resiliently contract to a lower stress configuration, thereby drawing opposing sides of puncture P together and closing the wound. A sealant, for example clip 54 of FIG. 2, may then be introduced to the closed puncture to seal the site closed, as discussed hereinabove. Alternatively, the sealing device may comprise RF current, supplied by an RF generator (not shown), applied across opposed tips 128, which act as bipolar electrodes.

Referring to FIGS. 6A-6E, as well as FIGS. 7A and 7B, a still further alternative embodiment of apparatus of the present invention is described. FIG. 6 depict the closure component of an integrated vascular device in use at vascular puncture P within vessel V. Apparatus 150 comprises sheath 152 coupled to a hub (not shown), closure component 154, and a closure actuator (not shown). Various closure actuators for use with closure component 154 will be apparent to those of skill in the art from the foregoing embodiments.

Sheath 152 may, for example, comprise an introducer sheath, a trocar, or a catheter, and includes central lumen 153 through which other devices may be introduced into the vasculature, for example, to perform a diagnostic or interventional procedure such as angiography, angioplasty, or stenting, or to seal a puncture site. Closure component 154 comprises spacer 156, needles 158, and needle cover 160. Spacer 156 is coaxially and slidably disposed about the exterior of sheath 152, and preferably has an annular diameter of about 1 mm to ensure that needles 158 engage the tissue surrounding puncture P rather than enter the puncture, so that the needles are able to draw the wound closed, as described hereinbelow. Needles 158 are disposed between spacer 156 and cover 160 during advancement to puncture P. Needles 158 comprise ledges 162, which act as positive stops to prevent excessive advancement of the needles with respect to cover 160, which comprises corresponding annular ledge 164. Cover 160 further comprises elastic segment 166, configured to elastically deform needles 158. Closure component 154 comprises at least two needles 158, and preferably comprises four. Needles 158 may further comprise retaining means (not shown), such as barbs or hooks, to assist in gripping tissue.

As shown in FIG. 6A, sheath 152 may be advanced through skin, fat, and muscle tissue into vessel V, through vascular puncture P, in accordance with well-known techniques. With closure component 154 in a proximal-most, fully retracted position adjacent the hub, an interventional procedure is performed through central lumen 153 of sheath 152 by introducing one or more interventional devices through the lumen into the patient's vasculature. Closure component 154 then is advanced via the closure actuator until it abuts against vessel V, as may be determined, for example, with a backbleed indicator, such as described for the foregoing embodiments. Cover 160 protects needles 158 and prevents snagging of tissue as closure component 154 is distally advanced down sheath 152 and through skin, fat, and muscle tissue. Spacer 156 retains needles 158 in a position away from the edge of puncture P.

In FIG. 6B, needles 158 are distally advanced with respect to needle cover 160 until ledge 162 abuts ledge 164. Needles 158 deflect elastic segment 166 of cover 160 outward and pierce tissue surrounding puncture P. FIG. 7A depicts, in isometric view, the segment of vessel V surrounding puncture P. With a needle arrangement comprising four needles 158, the needles create needle punctures N surrounding vascular puncture P. Sheath 152 and spacer 156 then are retracted proximally and removed from vessel V, as shown in FIG. 6C. As depicted in FIGS. 6D and 7B, elastic segment 166 of needle cover 160 resiliently contracts, thereby drawing needles 158 together and approximating the edges of the wound.

A sealant, such as a bioglue, tissue sealant, or clotting agent, then may be introduced to the puncture site to seal the wound closed. Alternatively, closure component 154 may be maintained in position until hemostasis occurs naturally, or sutures may be introduced through central lumen 153. In addition, or in the alternative, RF energy may be applied across needles 158, as described hereinabove with respect to FIG. 5, or a clip, such as clip 54 of sealing device 50 of FIG. 2, may be applied. Thermal energy from electrical induction, infrared light, ultrasonic vibration, microwave or laser irradiation, and other means may also be used to seal the puncture.

Illustratively, FIG. 6E depicts sealing device 170, comprising adhesive 172, being delivered through central lumen 153 within delivery sheath 174. After sufficient time for adhesive 172 to set, apparatus 150 is removed from vessel V.

Although preferred illustrative embodiments of the present invention are described hereinabove, it will be evident to one skilled in the art that various changes and modifications may be made without departing from the invention. It is intended in the appended claims to cover all such changes and modifications that fall within the true spirit and scope of the invention.

What is claimed is:

1. A method of closing an opening in tissue, comprising:
   disposing a sheath within a tissue tract, wherein a distal end of the sheath is disposed within an opening formed in tissue;
   performing a medical procedure through a lumen of the sheath;
   distally advancing at least two sharpened tips of a closure component to penetrate the tissue adjacent the opening from a proximal side toward a distal side of the tissue, the at least two sharpened tips having an expanded delivery configuration and a retracted deployed configuration to close the opening, the sharpened tips being associated with elastically deformed prongs;
   moving a distal end of a member within the closure component proximally past a distal end of the at least two sharpened tips to enable the elastically deformed prongs to resiliently contract towards each other to the retracted deployed configuration to close the opening; and
   applying a sealing means to the opening to effect closure of the opening.

2. The method according to claim 1, wherein the step of applying a sealing means comprises applying a sealing means selected from a group consisting of RF energy, thermal energy, electrical induction, infrared light, ultrasonic vibration, microwave or laser irradiation, clips, sutures, or adhesives.

3. The method according to claim 1, further comprising the step of delivering a sealant to the opening.

4. The method according to claim 1, further comprising the step of disposing a clip adjacent the opening to further seal the opening closed.

5. The method according to claim 1, wherein the closing step further comprises rotating the closure component after engaging the sharpened tips with the tissue.

6. A method of closing an opening in tissue, comprising:
   disposing a sheath within a tissue tract, wherein a distal end of the sheath is disposed within an opening formed in tissue;
   performing a medical procedure through a lumen of the sheath;
   distally advancing at least two sharpened tips of a distally-oriented closure component along a side of the sheath to penetrate the tissue, adjacent to the opening and proximal the distal end of the sheath from a proximal side to a distal side of the tissue, to close the opening, the at least two sharpened tips having an expanded delivery configuration and a retracted deployed configuration, the sharpened tips being associated with elastically deformed prongs;
   closing the opening formed in the tissue by moving a distal end of a member within the closure component proximally from a location distal the at least two sharpened tips past a distal end of the at least two sharpened tips to enable the elastically deformed prongs to resiliently contract towards each other to the retracted deployed configuration to close the opening; and
   applying a sealing means to the opening to effect closure of the opening.

7. The method according to claim 6, wherein distally advancing the closure component comprises sliding the closure component along the sheath until the at least two sharpened tips engage with tissue.

8. The method according to claim 6, wherein closing the opening comprises rotating the closure component about a longitudinal axis of the closure component after engaging the at least two sharpened tips with the tissue.

9. The method according to claim 6, further comprising the act of disposing a clip adjacent the opening to further seal the opening closed.

10. The method according to claim 6, further comprising the act of delivering a sealant to the opening.

11. A method of closing an opening in tissue, comprising:
    disposing a sheath within a tissue tract, the sheath comprising a proximal end, a distal end disposable within an opening formed in tissue, and a lumen extending from the proximal end toward the distal end;
    performing a medical procedure through the lumen of the sheath;
    distally advancing at least two sharpened tips of a distally-oriented closure component to penetrate the tissue adjacent to the opening, the at least two distally-oriented sharpened tips being advanced along a side of the sheath towards the distal end and being configured for engagement with tissue proximal the distal end of the sheath from a proximal side towards a distal side of the tissue, the distally-oriented sharpened tips having an expanded delivery configuration and a retracted deployed configuration;

moving a distal end of a member within the distally-oriented closure component proximally from a location distal the at least two sharpened tips past a distal end of the at least two sharpened tips to move the at least two distally-oriented sharpened tips towards one another to the retracted deployed configuration to close the opening;

wherein the at least two distally-oriented sharpened tips are associated with distally-oriented elastically deformed needles, and wherein moving the member releases the distally-oriented elastically deformed needles and moves the at least two distally-oriented sharpened tips towards one another to the retracted deployed configuration to close the opening; and applying a sealing means to the opening to effect closure of the opening.

12. The method according to claim 11, further comprising delivering a sealant to the opening.

13. The method according to claim 11, wherein closing the opening comprises rotating the closure component about a longitudinal axis of the closure component after engaging the at least two distally-oriented sharpened tips with the tissue.

14. The method according to claim 11, further comprising the act of disposing a clip adjacent the opening to further seal the opening closed.

15. The method according to claim 11, further comprising the act of delivering a sealant to the opening.

* * * * *